United States Patent
Jacobson et al.

(10) Patent No.: US 8,226,597 B2
(45) Date of Patent: Jul. 24, 2012

(54) FLUID DELIVERY SYSTEM AND FLOW CONTROL THEREFOR

(75) Inventors: James D. Jacobson, Lindenhurst, IL (US); Tuan Bui, Green Oaks, IL (US); Stephen R. Garchow, Libertyville, IL (US); Atif Yardimci, Northbrook, IL (US); James S. Slepicka, Spring Grove, IL (US)

(73) Assignee: Baxter International, Inc., Deerfield, IL (US)

( * ) Notice: Subject to any disclaimer, the term of this patent is extended or adjusted under 35 U.S.C. 154(b) by 937 days.

(21) Appl. No.: 12/053,156

(22) Filed: Mar. 21, 2008

(65) Prior Publication Data

US 2008/0243058 A1    Oct. 2, 2008

Related U.S. Application Data

(63) Continuation of application No. 11/333,594, filed on Jan. 17, 2006, now Pat. No. 7,879,025, which is a continuation of application No. 10/177,544, filed on Jun. 21, 2002, now abandoned.

(51) Int. Cl.
*A61M 31/00* (2006.01)

(52) U.S. Cl. .......................... 604/67; 604/151

(58) Field of Classification Search ............ 604/131, 604/890.1–892.1, 65–67, 151–155; 222/1; 73/261
See application file for complete search history.

(56) References Cited

U.S. PATENT DOCUMENTS

| | | | |
|---|---|---|---|
| 3,556,129 A | 1/1971 | Brown | |
| 3,590,886 A | 7/1971 | Judd | |
| 3,598,321 A | 8/1971 | Bobzin | |
| 3,604,386 A | 9/1971 | Turci | |
| 3,604,758 A | 9/1971 | Flain et al. | |
| 3,610,535 A | 10/1971 | Bradshaw | |
| 3,630,496 A | 12/1971 | Hurst et al. | |
| 3,632,232 A | 1/1972 | Tomita et al. | |
| 3,640,277 A | 2/1972 | Adelberg | |
| 3,655,296 A | 4/1972 | McDougall | |

(Continued)

FOREIGN PATENT DOCUMENTS

EP    0398583 A    11/1990

(Continued)

OTHER PUBLICATIONS

Madou, M.J., "Fundamentals of Microfabrication, The Science of Miniaturization," CRC Press LLC, 2002, pp. 340-341, Second Edition.

(Continued)

*Primary Examiner* — Kevin C Sirmons
*Assistant Examiner* — Phillip Gray
(74) *Attorney, Agent, or Firm* — K&L Gates LLP

(57) ABSTRACT

A fluid delivery system having a closed-loop control process for delivering a medical fluid to a patient. A fluid infusion system includes a pump for delivering a fluid to a patient via an administration tube. A flow sensor associated with the administration tube provides an indication of the actual flow rate of fluid in the administration tube. Such a flow sensor may comprise a positive displacement flow sensor constructed using micro-fabrication and/or micro-molding techniques. A reader reads the actual flow rate signal and provides an indication to a controller for controlling the pump. The flow rate information can also be used for providing status information, such as the existence of a blockage in the fluid delivery system.

21 Claims, 8 Drawing Sheets

U.S. PATENT DOCUMENTS

| | | | |
|---|---|---|---|
| 3,656,870 A | 4/1972 | Kusakabe et al. | |
| 3,667,464 A | 6/1972 | Alligood, Jr. | |
| 3,667,495 A | 6/1972 | Schuler et al. | |
| 3,677,248 A | 7/1972 | McPhee | |
| 3,692,050 A | 9/1972 | Deters | |
| 3,695,004 A | 10/1972 | DeLisio et al. | |
| 3,782,880 A | 1/1974 | Eubanks | |
| 3,785,459 A | 1/1974 | Patchen | |
| 3,786,649 A | 1/1974 | Kirschner | |
| 3,790,042 A | 2/1974 | McCormick et al. | |
| 3,794,245 A | 2/1974 | Wilson | |
| 3,797,492 A | 3/1974 | Place | |
| 3,807,446 A | 4/1974 | Driskell et al. | |
| 3,817,246 A | 6/1974 | Weigl | |
| 3,817,261 A | 6/1974 | Rogge | |
| 3,841,438 A | 10/1974 | Tine et al. | |
| 3,842,720 A | 10/1974 | Herr | |
| 3,846,052 A | 11/1974 | Scheibe | |
| 3,853,144 A | 12/1974 | Whelan | |
| 3,871,397 A | 3/1975 | Larsen | |
| 3,880,963 A | 4/1975 | Bier et al. | |
| 3,884,453 A | 5/1975 | Pearce et al. | |
| 3,892,071 A | 7/1975 | Garcea | |
| 3,905,362 A | 9/1975 | Eyrick et al. | |
| 3,910,311 A | 10/1975 | Wilke | |
| 3,929,157 A | 12/1975 | Serur | |
| 4,004,414 A | 1/1977 | Melchior et al. | |
| 4,018,362 A | 4/1977 | Ubaud | |
| 4,242,988 A | 1/1981 | Regamey | |
| 4,275,480 A | 6/1981 | Norton et al. | |
| 4,295,364 A | 10/1981 | Dooley et al. | |
| 4,296,809 A | 10/1981 | Tsai et al. | |
| 4,304,527 A | 12/1981 | Jewell et al. | |
| 4,306,441 A | 12/1981 | Dodson | |
| 4,313,499 A | 2/1982 | Tsai et al. | |
| 4,315,754 A | 2/1982 | Ruzicka et al. | |
| 4,318,214 A | 3/1982 | Dodson | |
| 4,328,820 A | 5/1982 | Serur | |
| 4,330,241 A | 5/1982 | Spurry | |
| 4,340,050 A | 7/1982 | Noiles | |
| 4,340,355 A | 7/1982 | Nelson et al. | |
| 4,347,824 A | 9/1982 | Pierson | |
| 4,350,301 A | 9/1982 | Erwin et al. | |
| 4,356,934 A | 11/1982 | Knake | |
| 4,368,688 A | 1/1983 | Grumer et al. | |
| 4,375,813 A | 3/1983 | Hessel | |
| 4,380,241 A | 4/1983 | Horsewell | |
| 4,387,734 A | 6/1983 | Borsanyi | |
| 4,396,002 A | 8/1983 | Lipets | |
| 4,405,103 A | 9/1983 | Eickmann | |
| 4,405,383 A | 9/1983 | Evertz et al. | |
| 4,411,935 A | 10/1983 | Anderson | |
| 4,414,253 A | 11/1983 | Grumer et al. | |
| 4,428,397 A | 1/1984 | Bron | |
| 4,430,180 A | 2/1984 | Shimizu | |
| 4,431,020 A | 2/1984 | Kowalski | |
| 4,431,425 A | 2/1984 | Thompson et al. | |
| 4,438,507 A | 3/1984 | Nakajima | |
| 4,452,273 A | 6/1984 | Hanzawa et al. | |
| 4,454,755 A | 6/1984 | Leunig | |
| 4,459,982 A | 7/1984 | Fry | |
| 4,468,220 A | 8/1984 | Willbanks | |
| 4,468,440 A | 8/1984 | Evjen | |
| 4,470,758 A | 9/1984 | Pazemenas et al. | |
| 4,474,309 A | 10/1984 | Solomon | |
| 4,477,231 A | 10/1984 | Swift | |
| 4,478,041 A | 10/1984 | Pollman | |
| 4,493,303 A | 1/1985 | Thompson et al. | |
| 4,498,843 A | 2/1985 | Schneider et al. | |
| 4,505,645 A | 3/1985 | Laguilharre | |
| 4,507,057 A | 3/1985 | Igarashi et al. | |
| 4,510,963 A | 4/1985 | Presley et al. | |
| 4,511,353 A | 4/1985 | Theeuwes | |
| 4,522,218 A | 6/1985 | Konak | |
| 4,543,044 A | 9/1985 | Simmons | |
| 4,545,317 A | 10/1985 | Richter et al. | |
| 4,552,017 A | 11/1985 | Biehle | |
| 4,552,555 A | 11/1985 | Theeuwes | |
| 4,564,331 A | 1/1986 | Karr-Ake | |
| 4,574,827 A | 3/1986 | Konak | |
| 4,586,922 A | 5/1986 | Theeuwes | |
| 4,612,964 A | 9/1986 | Durant | |
| 4,630,993 A | 12/1986 | Jensen | |
| 4,646,568 A | 3/1987 | Lew | |
| 4,754,603 A | 7/1988 | Rosman | |
| 4,755,172 A | 7/1988 | Baldwin | |
| 4,773,900 A | 9/1988 | Cochran | |
| 4,782,608 A | 11/1988 | Petrik | |
| 4,790,349 A | 12/1988 | Harris | |
| 4,793,807 A | 12/1988 | Friedman et al. | |
| 4,793,825 A | 12/1988 | Benjamin et al. | |
| 4,802,650 A | 2/1989 | Stricker | |
| 4,813,937 A | 3/1989 | Vaillancourt | |
| 4,823,551 A | 4/1989 | Hehl | |
| 4,828,218 A | 5/1989 | Medlock | |
| 4,828,705 A | 5/1989 | Thakore et al. | |
| 4,835,687 A | 5/1989 | Martin | |
| 4,836,157 A | 6/1989 | Miller | |
| 4,838,020 A | 6/1989 | Fujitsuka | |
| 4,838,257 A | 6/1989 | Hatch | |
| 4,838,860 A | 6/1989 | Groshong et al. | |
| 4,855,121 A | 8/1989 | Metzger | |
| 4,857,052 A | 8/1989 | Theeuwes | |
| 4,863,429 A | 9/1989 | Baldwin | |
| 4,865,088 A | 9/1989 | Stearns | |
| 4,867,063 A | 9/1989 | Baker et al. | |
| 4,867,743 A | 9/1989 | Vaillancourt | |
| 4,871,360 A | 10/1989 | Theeuwes | |
| 4,875,840 A | 10/1989 | Johnson et al. | |
| 4,883,327 A | 11/1989 | Farr | |
| 4,911,010 A | 3/1990 | Foran, Jr. et al. | |
| 4,919,596 A | 4/1990 | Slate et al. | |
| 4,921,547 A | 5/1990 | Kosarzecki | |
| 4,925,444 A | 5/1990 | Orkin et al. | |
| 4,926,852 A | 5/1990 | Zoltan et al. | |
| 4,928,656 A | 5/1990 | Ausiello | |
| 4,932,232 A | 6/1990 | Ballyns et al. | |
| 4,932,402 A | 6/1990 | Snook et al. | |
| 4,936,832 A | 6/1990 | Vaillancourt | |
| 4,938,212 A | 7/1990 | Snook et al. | |
| 4,941,809 A | 7/1990 | Pinkerton | |
| 4,966,691 A | 10/1990 | Brous | |
| 4,969,871 A | 11/1990 | Theeuwes et al. | |
| 4,969,872 A | 11/1990 | Urquhart et al. | |
| 4,972,878 A | 11/1990 | Carlin | |
| 4,979,644 A | 12/1990 | Meyer et al. | |
| 4,984,374 A | 1/1991 | Bird et al. | |
| 4,985,016 A | 1/1991 | Theeuwes et al. | |
| 4,985,017 A | 1/1991 | Theeuwes | |
| 4,994,031 A | 2/1991 | Theeuwes | |
| 5,009,251 A | 4/1991 | Pike et al. | |
| 5,019,055 A | 5/1991 | O'Boyle | |
| 5,023,057 A | 6/1991 | Metzger | |
| 5,029,620 A | 7/1991 | van Ditzhuijzen | |
| 5,150,612 A | 9/1992 | Lew | |
| 5,179,975 A | 1/1993 | Stevenson | |
| 5,184,519 A | 2/1993 | Ciarelli et al. | |
| 5,186,057 A | 2/1993 | Everhart | |
| 5,190,522 A | 3/1993 | Wojcicki et al. | |
| 5,203,503 A | 4/1993 | Cohen | |
| 5,205,722 A | 4/1993 | Hammond | |
| 5,205,819 A | 4/1993 | Ross et al. | |
| 5,207,642 A | 5/1993 | Orkin et al. | |
| 5,218,945 A | 6/1993 | Kapellen et al. | |
| 5,219,279 A | 6/1993 | Natwick et al. | |
| 5,220,517 A | 6/1993 | Sierk et al. | |
| RE34,365 E | 8/1993 | Theeuwes | |
| 5,232,434 A | 8/1993 | Inagaki et al. | |
| 5,234,265 A | 8/1993 | Tyler | |
| 5,244,353 A | 9/1993 | Paquet et al. | |
| 5,246,026 A | 9/1993 | Proudman | |
| 5,250,028 A | 10/1993 | Theeuwes et al. | |
| 5,251,149 A | 10/1993 | Williams et al. | |
| 5,251,785 A * | 10/1993 | Hayden et al. | 222/1 |
| 5,256,156 A | 10/1993 | Kern et al. | |
| 5,257,987 A | 11/1993 | Athayde et al. | |
| 5,275,043 A | 1/1994 | Cotton | |

| | | | | | | |
|---|---|---|---|---|---|---|
| 5,275,153 A | 1/1994 | Kay | | 5,722,956 A | 3/1998 | Sims et al. |
| 5,279,607 A | 1/1994 | Schentag et al. | | 5,724,824 A | 3/1998 | Parsons |
| 5,284,053 A | 2/1994 | Wadlow et al. | | 5,728,137 A | 3/1998 | Anderson-Fignon |
| 5,306,257 A | 4/1994 | Zdeb | | 5,730,712 A | 3/1998 | Falkvall et al. |
| 5,314,100 A | 5/1994 | Deaver | | 5,730,730 A | 3/1998 | Darling, Jr. |
| 5,318,540 A | 6/1994 | Athayde et al. | | 5,730,731 A | 3/1998 | Mollenauer et al. |
| 5,322,422 A | 6/1994 | Natwick et al. | | 5,735,268 A | 4/1998 | Chua et al. |
| 5,325,668 A | 7/1994 | Walchhutter et al. | | 5,743,252 A | 4/1998 | Rubsamen et al. |
| 5,325,715 A | 7/1994 | Foran, Jr. et al. | | 5,746,208 A | 5/1998 | Prince |
| 5,329,463 A | 7/1994 | Sierk et al. | | 5,751,300 A | 5/1998 | Cowger et al. |
| 5,348,231 A | 9/1994 | Arnold et al. | | 5,755,208 A | 5/1998 | Bombarda et al. |
| 5,351,914 A | 10/1994 | Nagao et al. | | 5,762,065 A | 6/1998 | Prince |
| 5,356,076 A | 10/1994 | Bishop | | 5,775,964 A | 7/1998 | Clark |
| 5,368,451 A | 11/1994 | Hammond | | 5,779,451 A | 7/1998 | Hatton |
| 5,370,612 A | 12/1994 | Maeda et al. | | 5,785,785 A | 7/1998 | Delmer et al. |
| 5,402,777 A | 4/1995 | Warring et al. | | 5,788,674 A | 8/1998 | McWilliams |
| 5,411,059 A | 5/1995 | Sever et al. | | 5,794,612 A | 8/1998 | Wachter et al. |
| 5,411,474 A | 5/1995 | Ott et al. | | 5,794,667 A | 8/1998 | Payne et al. |
| 5,415,041 A | 5/1995 | Foran, Jr. et al. | | 5,807,115 A | 9/1998 | Hu |
| 5,417,663 A | 5/1995 | Slettenmark | | 5,807,321 A | 9/1998 | Stoker et al. |
| 5,427,498 A | 6/1995 | Lehe et al. | | 5,810,323 A | 9/1998 | Winterer et al. |
| 5,444,733 A | 8/1995 | Coassin et al. | | 5,820,589 A | 10/1998 | Torgerson et al. |
| 5,447,586 A | 9/1995 | Tam | | 5,827,959 A | 10/1998 | Clanin |
| 5,447,672 A | 9/1995 | O'Neil | | 5,829,108 A | 11/1998 | DeCarbo, Sr. et al. |
| 5,450,336 A | 9/1995 | Rubsamen et al. | | 5,829,252 A | 11/1998 | Hirata et al. |
| 5,458,470 A | 10/1995 | Mannhart et al. | | 5,839,434 A | 11/1998 | Enterline |
| 5,460,490 A | 10/1995 | Carr et al. | | 5,855,756 A | 1/1999 | Anzalone, III |
| 5,460,500 A | 10/1995 | Geus et al. | | 5,868,159 A | 2/1999 | Loan et al. |
| 5,478,505 A | 12/1995 | McElfresh et al. | | 5,868,179 A | 2/1999 | Hartsell, Jr. |
| 5,482,841 A | 1/1996 | Buelow | | 5,876,675 A | 3/1999 | Kennedy |
| 5,492,534 A | 2/1996 | Athayde et al. | | 5,895,764 A | 4/1999 | Sklar et al. |
| 5,492,724 A | 2/1996 | Klinedinst et al. | | 5,906,597 A | 5/1999 | McPhee |
| 5,497,316 A | 3/1996 | Sierk et al. | | 5,906,682 A | 5/1999 | Bouras et al. |
| 5,503,626 A | 4/1996 | Goldrath | | 5,910,135 A | 6/1999 | Hadzic et al. |
| 5,504,306 A | 4/1996 | Russell et al. | | 5,911,506 A | 6/1999 | Nakamura et al. |
| 5,508,947 A | 4/1996 | Sierk et al. | | 5,921,428 A | 7/1999 | Rodgers |
| 5,509,791 A | 4/1996 | Turner | | 5,922,230 A | 7/1999 | Yokota |
| 5,513,636 A | 5/1996 | Palti | | 5,927,547 A | 7/1999 | Papen et al. |
| 5,527,493 A | 6/1996 | McElfresh et al. | | 5,932,091 A | 8/1999 | Tompkins et al. |
| 5,527,507 A | 6/1996 | Childers et al. | | 5,938,985 A | 8/1999 | Rodgers |
| 5,533,412 A | 7/1996 | Jerman et al. | | 5,944,255 A | 8/1999 | Shirmohamadi |
| 5,533,981 A | 7/1996 | Mandro et al. | | 5,954,695 A | 9/1999 | Sims et al. |
| 5,542,392 A | 8/1996 | Povinger | | 5,971,042 A | 10/1999 | Hartsell, Jr. |
| 5,553,619 A | 9/1996 | Prince | | RE36,378 E | 11/1999 | Mellette |
| 5,557,935 A | 9/1996 | Ganzel | | 5,980,489 A | 11/1999 | Krieslel |
| 5,564,305 A | 10/1996 | Cadeo | | 5,983,151 A | 11/1999 | Okada et al. |
| 5,566,660 A | 10/1996 | Camplin et al. | | 5,986,680 A | 11/1999 | Wen et al. |
| 5,567,243 A | 10/1996 | Foster et al. | | 5,992,230 A * | 11/1999 | Scarpa et al. .................. 73/261 |
| 5,578,752 A | 11/1996 | Schlecht et al. | | 5,993,420 A | 11/1999 | Hyman et al. |
| 5,580,585 A | 12/1996 | Holzschuh | | 6,019,115 A | 2/2000 | Sanders |
| 5,588,722 A | 12/1996 | Noguchi | | 6,020,651 A | 2/2000 | Nakamura et al. |
| 5,595,603 A | 1/1997 | Klinedinst et al. | | 6,050,143 A | 4/2000 | Smith |
| 5,595,640 A | 1/1997 | von Hoffmann | | 6,063,052 A | 5/2000 | Uber, III et al. |
| 5,608,647 A | 3/1997 | Rubsamen et al. | | 6,068,163 A | 5/2000 | Kihm |
| 5,617,456 A | 4/1997 | Kurosaki et al. | | 6,070,453 A | 6/2000 | Myers |
| 5,620,143 A | 4/1997 | Delmer et al. | | 6,073,860 A | 6/2000 | Coppock |
| 5,620,524 A | 4/1997 | Fan et al. | | 6,078,273 A | 6/2000 | Hutchins et al. |
| 5,624,409 A | 4/1997 | Seale | | 6,079,283 A | 6/2000 | Papen et al. |
| 5,628,305 A | 5/1997 | Melker | | 6,079,570 A | 6/2000 | Oppliger et al. |
| 5,632,444 A | 5/1997 | Camplin et al. | | 6,083,762 A | 7/2000 | Papen et al. |
| 5,640,435 A | 6/1997 | Kurosaki et al. | | 6,085,726 A | 7/2000 | Lei et al. |
| 5,648,052 A | 7/1997 | Schaefer et al. | | 6,085,742 A | 7/2000 | Wachter et al. |
| 5,657,254 A | 8/1997 | Sierk et al. | | 6,090,071 A | 7/2000 | Kriesel |
| 5,658,515 A | 8/1997 | Lee et al. | | 6,109,878 A | 8/2000 | Barton et al. |
| 5,662,087 A | 9/1997 | McCandless | | 6,112,605 A | 9/2000 | Papen et al. |
| 5,664,937 A | 9/1997 | Takahashi et al. | | 6,122,605 A | 9/2000 | Drees et al. |
| 5,671,918 A | 9/1997 | Hofmann et al. | | 6,135,967 A | 10/2000 | Fiorenza et al. |
| 5,672,103 A | 9/1997 | Jardinier | | 6,136,725 A | 10/2000 | Loan et al. |
| 5,672,167 A | 9/1997 | Athayde et al. | | 6,142,979 A | 11/2000 | McNally et al. |
| 5,673,562 A | 10/1997 | Friedt | | 6,143,077 A | 11/2000 | Ikeda et al. |
| 5,681,285 A | 10/1997 | Ford et al. | | 6,169,926 B1 | 1/2001 | Baker |
| 5,682,742 A | 11/1997 | Sato et al. | | 6,171,298 B1 | 1/2001 | Matsuura et al. |
| 5,683,149 A | 11/1997 | Aizawa et al. | | 6,183,461 B1 | 2/2001 | Matsuura et al. |
| 5,684,245 A | 11/1997 | Hinkle | | 6,193,704 B1 | 2/2001 | Winters |
| 5,694,764 A | 12/1997 | Blain et al. | | 6,202,645 B1 | 3/2001 | Brown |
| 5,695,127 A | 12/1997 | Delmer et al. | | 6,203,759 B1 | 3/2001 | Pelc et al. |
| 5,697,132 A | 12/1997 | DeCarbo, Sr. et al. | | 6,206,850 B1 | 3/2001 | O'Neil |
| 5,697,364 A | 12/1997 | Chua et al. | | 6,210,361 B1 | 4/2001 | Kamen et al. |
| 5,704,584 A | 1/1998 | Winterer et al. | | 6,212,959 B1 | 4/2001 | Perkins |

| | | |
|---|---|---|
| 6,213,986 B1 | 4/2001 | Darling, Jr. |
| 6,216,690 B1 | 4/2001 | Keitel et al. |
| 6,217,659 B1 | 4/2001 | Botelho et al. |
| 6,233,486 B1 | 5/2001 | Ekwall et al. |
| 6,234,997 B1 | 5/2001 | Kamen et al. |
| 6,235,635 B1 | 5/2001 | Roy |
| 6,243,600 B1 | 6/2001 | Prince |
| 6,247,061 B1 | 6/2001 | Douceur et al. |
| 6,250,151 B1 | 6/2001 | Tingleff et al. |
| 6,269,340 B1 | 7/2001 | Ford et al. |
| 6,366,840 B1 | 4/2002 | Buckley |
| 6,416,291 B1 | 7/2002 | Butterfield et al. |
| 6,740,059 B2 | 5/2004 | Flaherty |
| 6,802,811 B1 | 10/2004 | Slepian |
| 2003/0072647 A1 | 4/2003 | Lum |
| 2003/0073954 A1 | 4/2003 | Moberg et al. |
| 2003/0078534 A1 | 4/2003 | Hochman et al. |
| 2003/0171710 A1 | 9/2003 | Bassuk et al. |
| 2003/0171711 A1 | 9/2003 | Rohr et al. |

FOREIGN PATENT DOCUMENTS

| | | |
|---|---|---|
| EP | 409511 | 1/1991 |
| EP | 0409511 A | 1/1991 |
| EP | 0897690 A | 2/1999 |
| FR | 1299719 A | 12/1962 |
| GB | 2127179 A | 4/1984 |
| WO | 80/02377 | 11/1980 |
| WO | 8002377 A | 11/1980 |
| WO | 99/38552 | 8/1999 |
| WO | 00/61215 | 10/2000 |

OTHER PUBLICATIONS

Rai-Choudhury, P., Editor, "Electroplating in the Electronics Industry, Significance of Plating—Through-Mask Technology," Handbook of Microlithography, Micromachining, and Microfabricating, 1997, pp. 237-258, vol. 2.

* cited by examiner

FLUID DELIVERY SYSTEM AND FLOW CONTROL THEREFOR

PRIORITY CLAIM

This patent application is a continuation of U.S. application Ser. No. 11/333,594, filed on Jan. 17, 2006 now U.S. Pat. No. 7,879,025, which is a continuation of U.S. application Ser. No. 10/177,544, filed on Jun. 21, 2002 (now abandoned), the entire disclosure of which is incorporated herein by reference.

BACKGROUND OF THE INVENTION

1. Field of the Invention

The invention relates generally to delivering fluids to a patient and, particularly, to closed-loop flow control systems and methods for delivering medical fluids to a patient at a controlled delivery rate.

2. Description of the Prior Art

A variety of fluid delivery systems are currently being used in the medical field for delivering medical fluids (containing medication, nutrition, saline, and so on) to human and veterinary patients. It is often desirable to administer such medical fluids at relatively precise delivery rates. In some cases, the rate of delivery may be exceptionally important. In recent years, it has also been found to be advantageous to use various types of infusion pumps to administer medical fluids automatically, over extended periods of time. A typical infusion pump delivers the medical fluid into the patient's venous system using a delivery channel which usually comprises an administration tube (e.g., a polyvinyl chloride tube) connected to the patient using some form of catheter, needle, or the like.

Heretofore, infusion pumps and similar devices known in the art have typically not provided closed-loop flow control to achieve precise delivery rates. Rather, flow control has been open loop because actual flow rate information has not been used in controlling the infusion pump. A typical accuracy of such systems, in terms of flow rate, is normally no better than about +/−5%, and requires relatively sophisticated (and costly) mechanical components and tight material/geometry controls (e.g., of the tubing) to achieve that rate. In fact, ambulatory pumps typically achieve accuracies of +/−6-8%. Further, non-ambulatory pumps often do not achieve a five percent accuracy range at low flow rates or over longer time periods due to modification of the tubing material over time. For example, a typical peristaltic type pump requires repeated deformation of the administration tube. This deformation process changes the elastic recovery properties of the tube, resulting in changes in the volumetric output of the pump over time. One volumetric pump available from the assignee of the present application has a specified rating of +/−5% at 1-1200 ml/hr and +/−10% at 0.1-1 ml/hr. Another pump available from the assignee of the present application has a rated accuracy of +/−5% for the first 24 hours of use and +/10% thereafter.

While the foregoing accuracy ranges may be acceptable for some uses, greater accuracy is desirable for other uses. In some prior art systems, the pumping mechanism associated with the infusion pump is monitored and controlled, but the actual flow of fluid in the administration tube is not. For example, commonly assigned U.S. Pat. No. 5,533,981 describes a syringe infusion pump having a sensor for detecting the position and capture of a syringe plunger for use in controlling the dispensing of fluid from the syringe. Commonly assigned U.S. Pat. No. 6,078,273 discloses a variety of known infusion pump systems such as, for example, roller pump systems, peristaltic-type systems, valve-type systems, and motor driven systems. Further, commonly assigned U.S. Pat. No. 5,482,841 discloses a volumetric-type infusion pump. An example of an ambulatory infusion pump is a pump sold under the mark IPUMP by the assignee of the present application. An example of an ambulatory pump may also be found in U.S. Pat. No. 5,993,420.

Some systems have attempted to provide closed-loop control. For example, commonly assigned U.S. Pat. No. 5,533,412 discloses a pulsed thermal flow sensor. In such a system, the fluid is heated by a pulsed heating element. The fluid carries the thermal pulse through a flow channel to two sensor elements spaced apart, downstream from the heating element. The transit time of the thermal pulse between the two sensor elements provides an indication of the fluid flow velocity. Thus, such an approach requires the application of a heat pulse to the fluid in order to determine flow rate information.

Other prior art systems use information generated by positional encoders and decoders associated with a motor shaft to control an infusion pump. For example, the above-mentioned U.S. Pat. No. 6,078,273 discloses an encoder/decoder for use in controlling a medical infusion pump. While such systems reflect improvements in the art, they do not control fluid delivery in view of actual flow rates. In some circumstances, therefore, such systems would not provide as accurate information and tight control based on actual fluid flow rate data.

Sensors, such as positive displacement (PD) flow rate sensors, have been in use for many years and directly detect flow rates. A typical PD sensor includes two complementary rotating elements that, when exposed to a fluid flow, allow a relatively well-defined volume of the fluid to transfer from one side of the sensor to another side of the sensor with each rotation (or partial rotation) of the rotating elements. One advantage of PD sensors is that they support a variety of fluids with substantially equal levels of accuracy. In the prior art, such devices typically measure large fluid flow rates and the requisite level of precision is achieved by conventional precision machining and polishing techniques. In fact, components must sometimes be matched to ensure minimal clearances of the rotating elements and inner housing geometry. Such conventional PD sensors, however, are not well-suited for use in high-precision medical fluid delivery systems. For example, a commercial infusion pump may require the ability to deliver fluids over a wide range of delivery rates (e.g., 4 logs), including very low flow rates. Moreover, conventional manufacturing techniques tend to be expensive and, therefore, are not well-suited for use in manufacturing disposable items.

In recent years, fabrication techniques have developed that allow for the manufacture of micro-fabricated devices. Some of such devices are referred to as micro electro-mechanical system (MEMS) devices and micro molded devices. One technique for fabricating such devices is referred to in the art as LIGA processing. LIGA (Lithographie Galvanoformung Abormung) was developed in Germany in the late 1980s and translates roughly to the steps of lithography, electroplating, and replication. LIGA allows for the formation of relatively small, high aspect ratio components. Using this technique, a photoresist layer (e.g., an acrylic polymer such as polymethyl methacrylate (PMMA)) is applied to a metallized substrate material. The photoresist layer is selectively exposed to synchrotron radiation (high-energy X-ray radiation) via a mask pattern to form the desired high aspect ratio walls. Thus, the radiation "unzips" the PMMA backbone. The exposed sample is thereafter placed in a developing solution that selectively removes the exposed areas of PMMA. One development solution is 20% by volume of tetrahydro 1,4-oxazine, 5% by volume 2-aminoethanol-1, 60% by volume 2-(2-butoxyethoxy)ethanol, and 15% by volume water. The sample is thereafter electroplated; metal fills the gaps within the PMMA to form a negative image. The PMMA is then removed using a solvent, leaving a metal form for either immediate use or for use as a replication master. The entire LIGA process is described in greater detail in chapter 6, page 341 of Marc Madou, "The Fundamentals of Microfabrication, the Science of Miniaturization," Second Edition (CRC Press 2001).

LIGA has been identified for use in manufacturing microfabricated fluid pumps. It is believed, however, that LIGA-based micropumps have never been made available commercially. Cost is one substantial drawback of LIGA; it is believed that there are relatively few synchrotron devices (e.g., 10-15 devices) in the world. Accordingly, LIGA is fairly limited in its applicability for directly manufacturing low cost devices.

In view of the foregoing, an improved system and method for delivering a fluid to a patient is desired.

SUMMARY OF THE INVENTION

In one form, an improved fluid delivery system benefits from a closed-loop control process that uses flow rate information to ensure that the desired flow rate is substantially achieved. Further, in one form, such a system is constructed using one or more micro-fabrication and/or molding techniques allowing for a cost-effective, disposable administration set.

Briefly described, a system for delivering fluid at a desired flow rate from a reservoir to a delivery point associated with a patient, embodying aspects of the invention, includes a delivery channel between the reservoir and the delivery point through which the fluid is delivered to the patient. A pump is associated with the delivery channel for operatively delivering the fluid to the delivery point at an adjustable output rate. A flow sensor is located along the delivery channel for sensing a flow of the fluid in the delivery channel and for generating a flow rate signal indicative of a rate of flow of the fluid in the delivery channel. The flow sensor comprises a positive displacement flow sensor. A controller controls the pump. The controller causes adjustments to the output rate of the pump as a function of the flow rate signal whereby the desired flow rate is substantially achieved.

In another aspect, the invention relates to a closed-loop fluid delivery system for delivering a fluid from a reservoir to a delivery point associated with a patient at a desired delivery rate via an administration tube. The closed-loop fluid delivery system includes fluid delivery means located along the administration tube for operatively supplying the fluid to the delivery point at a controllable output rate. A positive displacement flow sensing means is located between the fluid delivery means and the delivery point for sensing an actual flow rate of the fluid in the delivery channel and for generating a flow rate signal indicative of the actual flow rate of the fluid in the delivery channel. A control means associated with the fluid delivery means receives and is responsive to the flow rate signal for adjusting the output rate of the fluid delivery means such that the desired delivery rate at which the fluid is supplied to the delivery point associated with the patient is substantially achieved.

In still another aspect, the invention relates to a system for delivering a fluid from a reservoir to a delivery point associated with a patient at a desired delivery rate via an administration tube. The system includes a delivery mechanism operatively connected between the reservoir and the delivery point. The delivery mechanism is constructed and arranged for selectively delivering the fluid to the delivery point via the administration tube at a controllable output flow rate. A closed-loop control system controls the output flow rate of the delivery mechanism. The closed-loop control system includes a positive displacement flow sensor connected in-line with the administration tube for determining an actual flow rate of the fluid in the administration tube and for providing an flow rate indication reflecting the actual flow rate. A reader associated with the positive displacement flow sensor receives the flow rate indication and provides a flow control signal reflecting the flow rate indication. A controller associated with the delivery mechanism receives and is responsive to the flow control signal for controlling the output flow rate of the delivery mechanism as a function of the flow control signal such that the output flow rate is substantially equal to the desired delivery rate.

In yet another aspect, the invention relates to a method of delivering a medical fluid to a delivery point associated with a patient at a desired delivery flow rate. The method includes operatively connecting a reservoir to a delivery mechanism. The reservoir contains the medical fluid to be delivered to the delivery point. The delivery mechanism is operatively connected to an administration tube. The administration tube is in fluid communication with the delivery point. The delivery mechanism receives the medical fluid from the reservoir and supplies the medical fluid to the delivery point via the administration tube at an output flow rate. The output flow rate of the medical fluid in the administration tube is sensed using a positive displacement flow sensor. The sensed output flow rate of the medical fluid is compared with the desired delivery flow rate. The delivery mechanism is controlled such that the output flow rate substantially corresponds to the desired delivery flow rate.

In another aspect, the invention relates to a closed-loop flow control system for controlling a medical fluid delivery system. The medical fluid delivery system delivers a fluid from a reservoir to a delivery point associated with a patient at a desired delivery rate via an administration tube. The medical fluid delivery system includes a delivery mechanism operatively connected between the reservoir and the delivery point. The delivery mechanism is constructed and arranged for delivering the fluid to the delivery point via the administration tube at a controllable output flow rate. The closed-loop flow control system includes a positive displacement flow sensor connected in-line with the administration tube for determining an actual flow rate of the fluid in the administration tube and for providing an flow rate indication reflecting the actual flow rate. A reader associated with the positive displacement flow sensor receives the flow rate indication and provides a flow control signal reflecting the flow rate indication. A controller associated with the delivery mechanism receives and is responsive to the flow control signal for controlling the output flow rate of the delivery mechanism as a function of the flow control signal such that the output flow rate is substantially equal to the desired delivery rate.

In still another aspect, the invention relates to a method of detecting a blockage in a medical fluid delivery system arranged for delivering a medical fluid to a delivery point associated with a patient at a desired flow rate. The method includes operatively connecting a reservoir to a delivery mechanism. The reservoir contains the medical fluid to be delivered to the delivery point. The delivery mechanism is operatively connected to an administration tube that is in fluid communication with the delivery point. The delivery mechanism receives the medical fluid from the reservoir and supplies the medical fluid to the delivery point via the administration tube at an output flow rate. The output flow rate of the medical fluid in the administration tube is sensed. A determination is made whether the sensed output flow rate is indicative of a blockage in the administration tube. An alarm signal is provided if it is determined that the sensed output flow rate indicates that the administration tube is blocked.

In yet another aspect, the invention relates to an administration set for use in connection with a fluid delivery system that is arranged for delivering a fluid from a reservoir to a delivery point associated with a patient at a desired delivery rate. The fluid delivery system includes a pump having an output rate for delivering fluid from the reservoir to the delivery point and a controller for adjusting the output rate of the pump such that the desired delivery rate is substantially achieved. The administration set includes an administration tube for providing fluid communication between the reservoir and the delivery point. A positive displacement flow sensor is located along the administration tube and is sized and shaped for being positioned in fluid communication with the fluid within the administration tube. The positive displacement flow sensor senses a rate of flow of the fluid in the administration tube and generates a flow rate signal that is indicative of the sensed rate of flow of the fluid in the administration tube such that the controller adjusts the output rate of the pump as a function of the flow rate signal.

In another form, the invention relates to a positive displacement flow sensor for use in connection with a medical fluid infusion system that includes an administration set having an administration tube. The positive displacement flow sensor comprises a housing having an inlet port and an outlet port. The inlet and outlet ports are operatively connected to the administration tube. A first rotor is positioned within the housing between the inlet port and the outlet port. A second rotor is positioned within the housing between the inlet port and the outlet port. The second rotor is positioned adjacent to the first rotor, and the first and second rotors are constructed and arranged to rotate in response to a flow of medical fluid in the administration tube for detecting flow of the medical fluid in the administration tube. A cover encloses the housing such that when the medical fluid flows into the inlet port it causes the first rotor to rotate and thereafter the medical fluid exits through the outlet port.

Alternatively, the invention may comprise various other devices, methods, and systems.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION OF PREFERRED EMBODIMENTS

Figure 1:
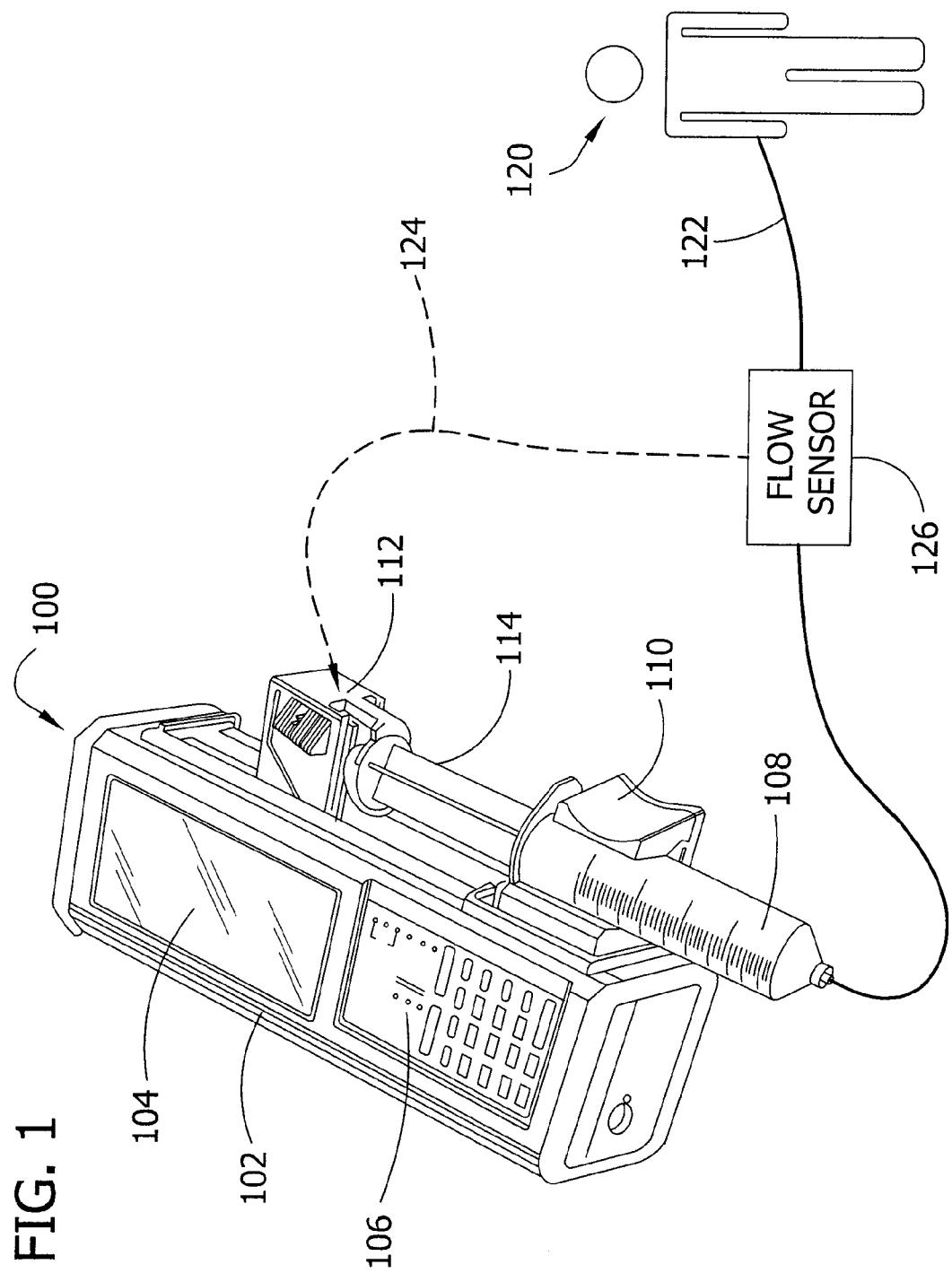
FIG. 1 illustrates one embodiment of an infusion pump suitable for use in connection with aspects of the invention.

Referring now to the drawings, FIG. 1 illustrates one embodiment of an infusion pump 100 suitable for use in connection with aspects of the present invention. In the illustrated example, the infusion pump 100 comprises a syringe-type infusion pump. Infusion pump 100 includes a housing 102, a display screen 104, and a control panel 106. The control panel 106 and the display screen are used to enter set-point data for operating infusion pump 100 and for monitoring the operation of pump 100.

The infusion pump 100 also includes a syringe barrel 108 for holding a medical fluid to be administered. A barrel bracket 110 attaches the syringe barrel 108 is attached to the housing 102. A movable syringe driver 112 is also attached to housing 102 and is positioned in engagement with a syringe plunger 114. A driving mechanism within housing 102 is constructed and arranged so that the movable syringe driver 112 can drive syringe plunger 114 into: (or out of) syringe barrel 108 in a controlled direction along barrel 108.

Operationally, a user loads a desired amount of the fluid to be administered into syringe barrel 108. Syringe barrel 108 is mounted to housing 102 via bracket 110 and plunger 114 is moved into position within barrel 108. Infusion pump 100 is attached to a patient 120 (e.g., a human patient or a veterinary patient) via a channel such as an intravenous PVC administration tube 122. The user enters the desired administration program on control panel 106 and infusion pump 100 controls a movement of plunger 114 via driver 112 to deliver the fluid to the patient at a programmed delivery rate corresponding to the administration program.

To this point, the description of infusion pump 100 and its operation in connection with patient 120 has been generally in accordance with known infusion systems. In other words, fluid delivery is controlled in an open-loop fashion-based on a desired set point without regard to actual flow rates. Line 124 diagrammatically illustrates a closed-loop information feedback path from a flow rate sensor 126 that is positioned for detecting a flow rate in tube 122 at a point between infusion pump 100 and patient 120. Closed loop control using such flow information in a feedback path is discussed in greater detail in connection with FIG. 2. Also, and as also discussed in greater detail below, aspects of a sensed flow information feedback system can be used for occlusion detection instead of or in addition to flow rate control.

Figure 2:
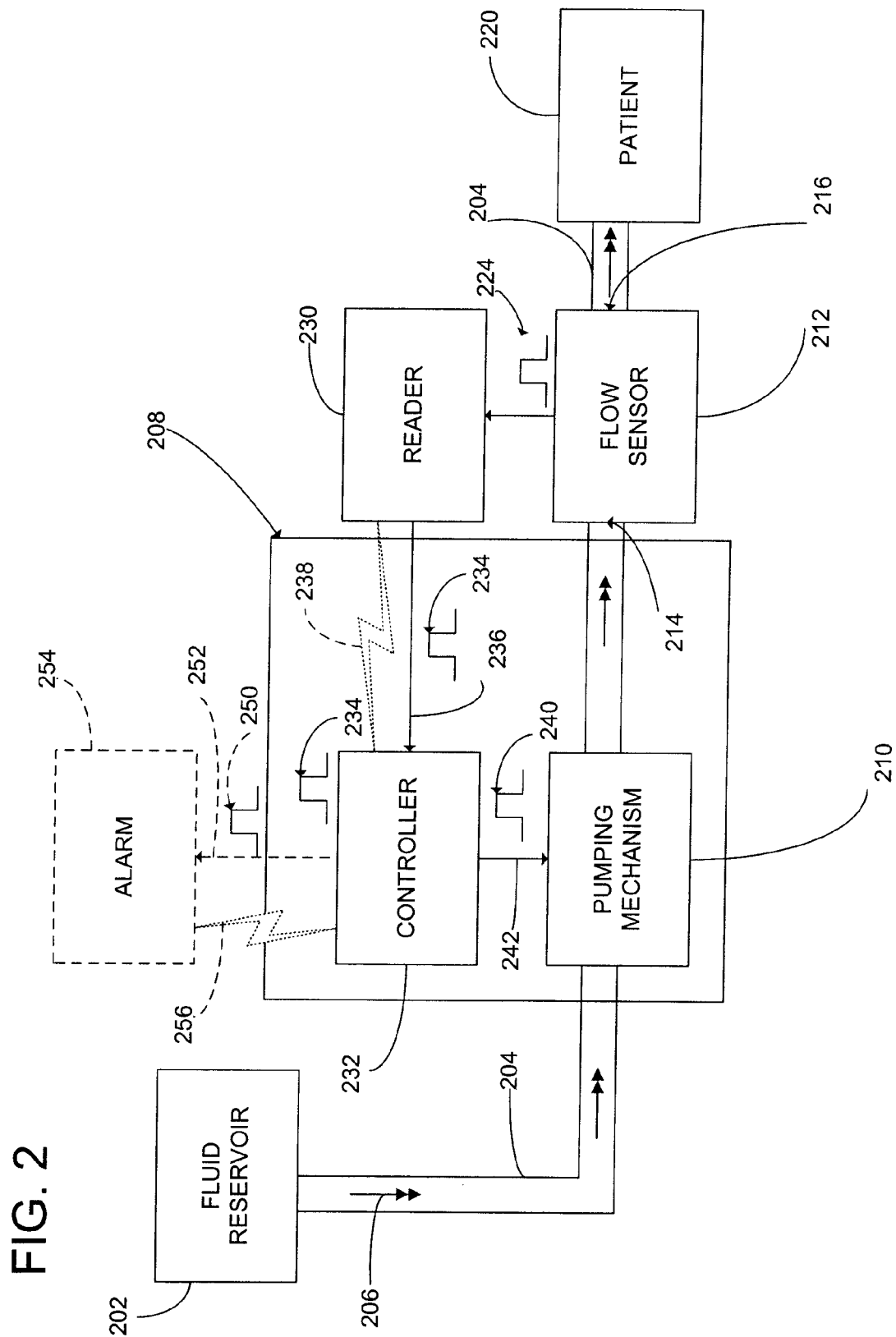
FIG. 2 is a block diagram of one embodiment of a closed-loop flow control system suitable for use in connection with an medical fluid infusion pump, such as the infusion pump of FIG. 1, according to aspects of the invention.

FIG. 2 is a block diagram that schematically illustrates one embodiment of a closed-loop flow control system suitable for use in connection with an medical fluid infusion pump, such as a volumetric or ambulatory type pump. It should be understood that a syringe pump does not "draw" from a reservoir.

Rather, as shown in FIG. 1, the plunger of a syringe pump acts upon the reservoir to output fluid to the patient. For present purposes, such differences between a syringe type pumps and volumetric and ambulatory type pumps are not substantial, and aspects of the invention may be employed with each of these types of infusion pumps.

In particular, FIG. 2 illustrates a fluid reservoir 202 connected to an administration tube 204. Arrows 206 indicate that a fluid flows in the administration tube 204 into the patient. Administration tube 204 is operatively connected to an infusion pump system 208 that is positioned along the administration tube 204. It should be understood that the position of the infusion pump system 208 and the nature and type of connection between infusion pump 208 and administration tube 204 will often depend, at least in part, on the particular type of infusion pump used. In the illustrated embodiment infusion pump 208 includes a pumping delivery mechanism 210. As will be explained in more detail below, there are a variety of pumping mechanisms that may be employed. For example, the pumping mechanism 210 may comprise a syringe driver driving a syringe plunger in a syringe-type infusion pump. For present purposes, it is sufficient to note that the pumping mechanism 210 is controllable/adjustable for controlling/adjusting a flow rate of the fluid within administration tube 204 to conform with a desired flow rate.

A flow rate sensor 212 is located in-line with administration tube 204 and receives the fluid through pumping mechanism 210. The flow rate sensor 212 preferably includes an inlet port 214 and an outlet port 216. The inlet port 214 receives flowing fluid at the flow rate provided by pumping mechanism 210 and provides flowing fluid at its output port 216. In one embodiment, administration tube 204 comprises a plurality of IV tube pieces. A first piece of IV tube connects pumping mechanism 210 to input port 214 and a second piece of IV tube connects output port 216 to a delivery point associated with a patient 220. Other flow sensing arrangements are possible. For example, flow rate sensor 212 could be located entirely within the IV tube.

It should be understood that, in a typical continuous infusion pump, fluid runs from a reservoir to an access device through an administration set flow rate may be measured at any convenient point along the path because the flow rate is the same—upstream or downstream of the pump. For example, the flow rate in administration tube 204 of FIG. 2 just below fluid reservoir 202 is equal to the flow rate at input port 214, as. well as at output port 216. Some infusion pumps (e.g., metering and discontinuous systems), however, fill a defined volume of fluid from a reservoir, and thereafter pump that fluid out, over time, according to the delivery profile. Further, an amount of compliance may exist within a disposable administration set. Therefore, in many applications there will be value in locating the flow rate sensor downstream of the pump, and closer to the patient.

In one embodiment, fluid reservoir 202, tube 204 and flow rate sensor 212 comprise part of a disposable administration set that is mounted in infusion pump system 208. It should be understood that a disposable set could include a variety of components including, for example, valves (e.g., normally closed valves), specialized pumping complements, and the like. Further, the set can include a reservoir; or the reservoir can be separate and integrated with the set through a spike or other connection.

The flow rate sensor 212 provides an indication of an actual rate of flow within administration tube 204. In one embodiment, flow rate sensor 212 is a positive displacement flow sensor for providing a flow rate signal 224 representing the actual flow rate of fluid flowing in administration tube 204. It is to be understood that there are a variety of ways that flow rate sensor 212 could provide the flow rate signal 224. For example, flow rate sensor 212 can be constructed such that a varying optical contrast or electrical signal is generated by the flow of fluid. Exemplary structures and methods for providing such a flow rate. Signal are discussed in greater detail below. Further, in one embodiment, flow rate sensor 212 comprises a passive device, having no electrical connections thereto.

A reader 230, such as an optical or electrical signal detector, is Preferably positioned adjacent flow rate sensor 212 such that it can receive/detect flow rate signal 224. In turn, the reader 230 communicates the detected flow rate signal 224 to a controller 232 via a communication path. In particular, reader 230 receives flow rate signal 224 from flow rate sensor 212 and supplies a flow-control signal 234 to the controller 232. It should be understood that the flow control signal 234 preferably provides substantially the same information as the flow rate signal 224 an indication of the actual flow rate of fluid in tube 204. For example, in one embodiment, the flow control signal 234 comprises one or more pulses. In such an embodiment, controller 232 is programmed to interpret each pulse as corresponding to a fixed volume of fluid flowing through sensor 216. Accordingly, controller 232 can determine the actual flow rate sensed in the administration tube as a function of the number of pulses received from reader 230. In such an embodiment, an indication of the cumulative flow volume delivered is provided by the number of pulses, and an indication of the instantaneous flow rate is determined by the time period of the pulses.

In one embodiment, the communication path between reader 230 and controller 232 comprises a wired communication channel 236 In another embodiment, the communication path comprises a wireless (e.g., IR, RF, and/or the like) communication channel 238. The wireless channel 238 may be advantageous, for instance, in systems in which flow rate sensor 212 and/or reader 230 are located at a distance from controller 232 and/or when physical connectivity is undesirable. One exemplary wireless communication channel uses Bluetooth™ wireless technology. Bluetooth™ is a wireless specification from a trade association, Bluetooth SIG, Inc. In general, it is a low cost and low power specification, operating in the unlicensed 2.4 GHz spectrum, and using spread spectrum frequency hopping techniques.

The controller 232 is operatively connected for automatically controlling pumping mechanism 210. This is illustrated schematically as a pump control signal 240 on line 242 between controller 232 and pump 210. It should be understood that a wide variety of devices may serve as controller 232. For example, controller 232 may be embodied by a processor (e.g., a microprocessor or microcontroller), discrete logic components, application specific circuitry, programmable logic devices, analog circuitry, or combinations thereof. Further a motor-based pump could be controlled by adjusting the motor rotation rate or a cycle time associated with the motor. If a certain type of MEMS-based pump is employed. for example, control may be achieved by adjusting the frequency of a piezo oscillation.

The system can also be configured to provide a status signal. For example, controller 232 provides a status signal, such as an alarm signal 250, on a line 252 (and/or a wireless channel 256) to a status monitoring device 254. In one form, the status monitoring device 254 comprises an audible alarm system for providing an audible alarm in the event of a malfunction. Status monitoring device 254 may also comprise other audio, visual, audio-visual, and vibrating devices such as, for example, CRT monitors, pagers, horns, buzzers, speakers, computers, portable telephones (e.g., cellular telephones), personal digital assistants (PDAs), and the like. By way of one specific example, controller 232 provides an alarm signal to cause an audible and/or visual alarm to be activated if controller 232 is unable to control pump 210 to achieve a desired flow rate. Such a condition can occur if an occlusion or blockage in administration tube 204 prevents an adequate flow of fluid to patient 220. Such a blockage may include complete blockages, as well as partial blockages affecting flow rate. Alarm conditions can be programmed to occur for a variety of other reasons, such as when the fluid supply in reservoir 202 becomes depleted to a level at which pump 210 can no longer deliver the fluid at the desired delivery rate. It should be appreciated, however, that status indications other than failures or improper operational conditions may also be provided. For example, a status signal could be used to provide an indication at a remote monitoring station of the current sensed flow rate or another indication regarding the operation of the system. Similarly, sensed flow rate information can be used to anticipate when the fluid supply will be depleted, such that a suitable indication is provided in advance of such event.

An operational example of the closed-loop flow control system of FIG. 2 is now described. A patient is operatively connected to administration tube 204 (e.g., via a catheter inserted at a desired delivery point associated with the patient). Reservoir 202 contains a fluid to be administered to the patient and is operatively connected to administration tube 204 and pumping mechanism 210. A desired delivery rate is entered on a control panel associated with the pump (see, e.g., FIG. 1). In FIG. 1, for example, it is to be understood that control panel 106 and display 104 cooperate to provide a user interface to facilitate entering set-point data for use by pump 100. In the present embodiment, controller 232 uses set-point data representative of the desired delivery rate in combination with the flow control signal 234 far controlling the system.

As pump 210 causes the fluid to be delivered to patient 220 via tube 204, flow rate sensor 212 senses the flow rate of the fluid in tube 204 and periodically (or continuously) outputs flow rate signal 224 which is received/detected by reader 230. For example, if flow rate sensor 212 is constructed and arranged to provide an optical signal indication of the actual flow rate of fluid, reader 230 comprises an optical reader for detecting the optical signal indication generated by flow rate sensor 212. As a further example, in one embodiment reader 230 illuminates flow rate sensor 212 with a light and examines the light reflected by the flow rate sensor to determine the flow rate signal 224.

Reader 230 thereafter provides flow control signal 234 to controller 232. This flow control signal 234 is functionally related to the flow rate signal 224 and, therefore, provides an indication of the actual flow rate of fluid into patient 220. As such, controller 232 is able to monitor the actual flow rate of fluid in tube 204. With this information, controller 232 is able complete a closed-loop control path with pump 210. In other words, controller 232 executes a control scheme for generating the pump control signal 240 to adjust the pumping action of pump 210 so that the actual flow rate, as measured by flow rate sensor 212, more closely matches the desired flow rate. It should be understood that a variety of control schemes may be employed, depending upon goals. For example, in some applications it may be desirable to control the pump to provide a high degree of accuracy in terms of instantaneous flow rate. In other applications, it may be desirable to control the pump in terms of the total volume of fluid infused. In still other applications, it may be desirable to optimize control in terms of both instantaneous flow rate and total volume. Other variations are possible.

The degree of accuracy with respect to controlling flow rate can be varied, depending upon usage For example, if gross accuracy (e.g., +/−15%) is acceptable, the closed-loop feedback control could be disabled in software (e.g., via a control panel input) or by eliminating flow rate sensor 212 from the administration set. Gross accuracy can also be achieved by adjusting control parameters, such as sample rates and so on. On the other hand, if a relatively high degree of accuracy is desired (e.g., +/−2%), the controller is preferably programmed/configured to tightly control the pumping action of pump 210. It should be appreciated, therefore, that an infusion pump system, embodying aspects of the invention can be reconfigured to accommodate a wide variety of needs, thereby improving the usefulness of such a system.

As explained above, such a closed-loop flow control system has been heretofore unknown in the art. Among the advantages of such a system is the ability to more closely control the flow of fluid to patient 220. In some situations, a particular precise flow rate is valuable. Further, flow rate sensor 212 is compatible with a wide variety of fluid delivery profiles, including constant profiles, pulsatile profiles, and other time-varying and non-uniform delivery profiles. With such profiles, including pulsatile flow profiles, the pump may need to ramp up and/or down from its running rate faster than with other delivery profiles. Thus, knowledge of actual flow rate helps to ensure tighter control of the profile. For example, controller 232 can monitor the actual flow rate in tube 204 (as detected by flow rate-sensor 212) over time and control the pumping action of pump 210 to ensure that the actual flow rate conforms to the desired delivery profile. Moreover, closed-loop control allows infusion pumps to be manufactured with a greater degree of flexibility in terms of manufacturing tolerances and the like. In some prior art systems, delivery accuracy is attempted by tightly controlling the tolerances of the mechanical pumping components and mechanisms, which can be expensive. With flow rate feedback control according to aspects of the invention, on the other hand, infusion pumps can be made with less precise (and therefore less expensive) components and mechanisms, yet still achieve a high degree of accuracy in terms of fluid delivery rate control.

It should be further appreciated that the tubing would not need to be as precise and the integration of the pump and disposable components would be less dependent upon the materials used in. the disposable components. For example, PVC tubing provides certain advantages in prior art systems, so the design of the infusion pump may need to be tailored to be compatible with such tubing. This type of engineering expense may be eliminated if PVC tubing is no longer necessary.

Further, knowing the actual rate of flow in tube 204 with a relatively high degree of precision also allows the system to provide a highly accurate and fast occlusion detection capability. If should be appreciated that a blockage a complete blockage and/or a partial blockage between the fluid reservoir and the delivery point can result in an unacceptably low rate of flow. Such blockages are sometimes referred to herein as occlusions but may be caused by a variety of conditions, including a kink in tube 204. Prior art attempts to detect occlusions rely on pressure sensing, which requires a relatively large change in the pressure in the tube to be detected. A disadvantage of pressure sensing is that it may take a long time for the pressure in the tubing to increase to a detectable level. This is especially true when delivering fluids at a relatively low delivery rate. For example, a blockage (e.g., a complete and/or partial blockage) associated with a 0.1 ml/hour delivery rate could take two hours or more to be detected with a typical prior art pump. Further, if the sensitivity of a pressure sensing system is increased to reduce response times, more false alarms are likely to be experienced.

In contrast, a closed-loop flow controller according to aspects of the present invention is able to rapidly detect blockages (complete and/or non-complete blockages, even at very low delivery rates) because flow rate sensor 212 detects an actual flow rate and does not require a pressure build up. One embodiment of flow rate sensor 212 is capable of providing accurate measurements (e.g., better than +/−5%)—over four logs of range. For example, a pump using such a flow sensor supplies fluid frond about 0.1 ml/hr up to about 2000 ml/hr. Thus, flow rate sensing. and occlusion detection is possible at low-flow rates, as well as at higher flow rates.

For convenience, the foregoing descriptions of FIGS. 1 and 2 have been generally provided in terms of embodiments comprising syringe-type infusion pumps and ambulatory and volumetric pumps. One type of prior art syringe pump is more fully described-in commonly assigned. U.S. Pat. No. 5,533,981. It should be understood that, with the benefit of the present disclosure, closed loop control systems and methods may be adapted for use with other types of medical fluid delivery systems. Such systems include, for example, rotary and linear peristaltic-type pump systems, valve-type pump systems, piezoelectric pump systems, pressure-based pump systems, and various motor and/or valve driven systems.

A peristaltic-type pump manipulates the IV administration tube to achieve a desired flow rate. In one embodiment, a peristaltic-type pump employs an array of cams or similar devices that are angularly spaced from each other. The cams drive cam followers that are connected to pressure fingers. These elements cooperate to impart a linear wave motion on the pressure fingers to apply force to the IV tube. This force imparts motion to the fluid in the IV tube, thereby propelling the fluid. Other forms of peristaltic-type pumps use different pressure means such as, for example, rollers.

Some valve-type pumps employ pumping chambers and upstream and downstream valving (e.g., electronically controlled valves) to sequentially impart a propulsion force to the fluid to be delivered to the patient. It is also possible to use a valve in connection with a gravity-fed delivery system in which gravity provides the motivating force and one or more valves are used to control the flow rate. Piezoelectric pumps control pumping by varying the magnitude of an applied voltage step. Pressure-based pumps adjust flow rate by controlling the pressure applied to a fluid reservoir (sometimes called "bag squeezer" systems).

Further, the closed-loop control systems and methods described herein may be used in ambulatory infusion pump systems and volumetric infusion pump systems. It should also be understood that the components illustrated in FIG. 2 are grouped for Convenience. For example, the status monitor device 254 could be made integral with the rest of the, infusion pump system 208: Likewise, reservoir 202 could be integral with the pump unit or Separate. For example, in a syringe pump, the barrel of the syringe acts as a reservoir, but is physically mounted to the infusion pump housing. In other words, with syringe pumps and pressure-based pumps, the reservoir is typically contained within the pump boundaries. With a volumetric or ambulatory pump, the reservoir is generally more external to the pump boundaries.

Figure 3A:
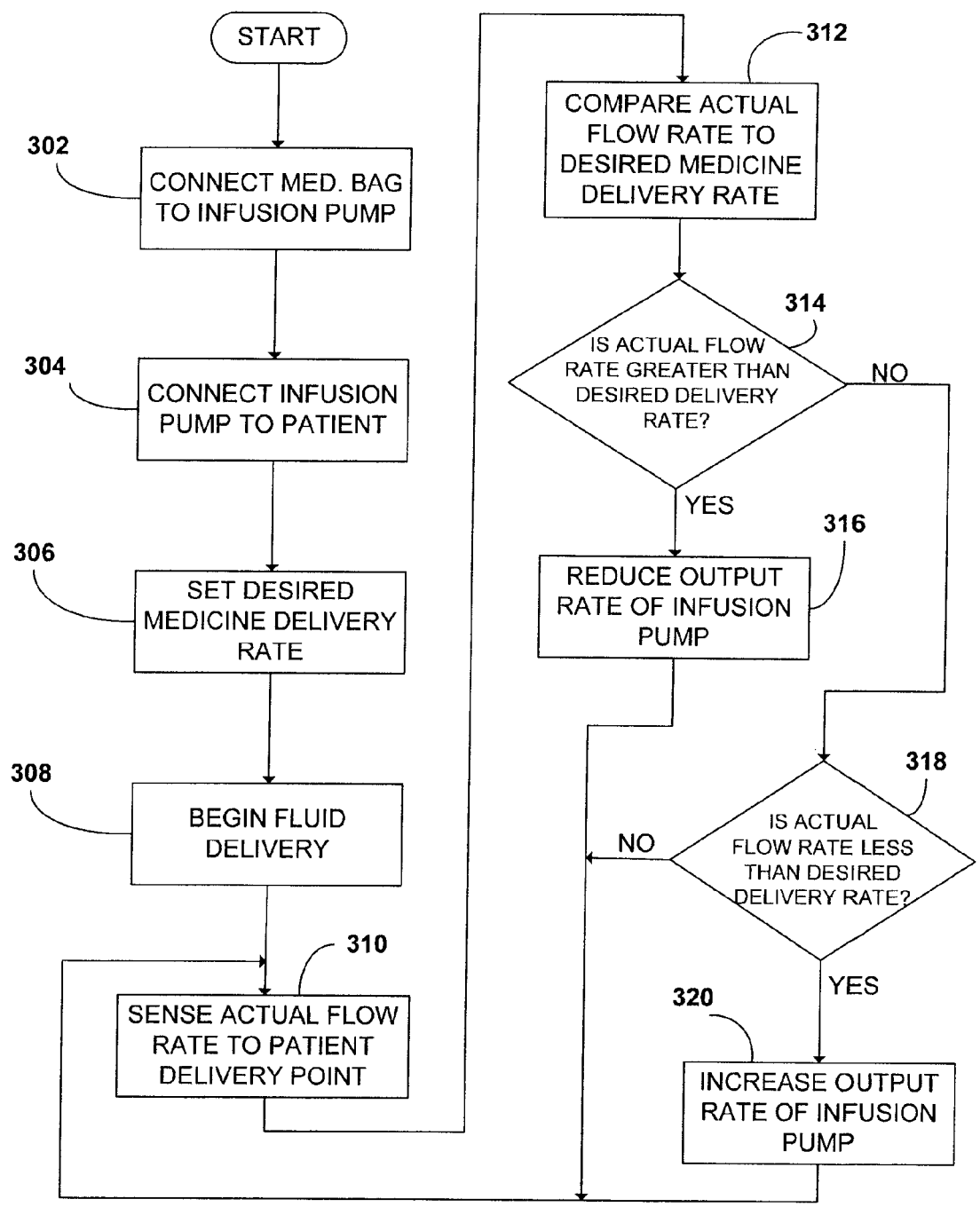
FIG. 3A is a flow chart that illustrates an exemplary method of delivering a fluid to a patient in accordance with a closed-loop flow control process, suitable for use in connection with aspects of the invention.

FIG. 3A is a flow chart that illustrates an exemplary method of delivering a fluid to a patient in accordance with a closed-loop flow control process. As illustrated therein, a fluid reservoir (e.g., a fluid bag) is connected to an infusion pump which, in turn, is connected to the patient (blocks 302, 304). After a desired delivery rate is selected (block 306), fluid delivery begins (block 308). Periodically. (or continuously) the actual flow rate of fluid to a delivery point associated with the patient is sensed. (block 310). For example, and, as explained above, a positive displacement flow rate sensor located in-line between the patient and the pump can be used to sense actual fluid flow and provide a flow rate indication to a control device. The actual flow rate is compared to the desired delivery rate at block 312. If the actual flow rate is appreciably greater than desired (block 314), the infusion pump is adjusted such that its output rate is reduced (block 316), thereby reducing the actual delivery rate to more closely match the desired flow rate. If, however, the actual flow rate is appreciably less than the desired rate (block 318), the infusion pump is adjusted such that its output rate is increased (block 320), thereby increasing the actual delivery rate.

In one embodiment, the method also includes using a disposable administration-set that includes, for example, an administration tube and an in-line flow rate sensor (e.g., tube 204 and flow rate sensor 212 of FIG. 2) such that, upon completing the fluid delivery process, the administration set is discarded.

Figure 3B:
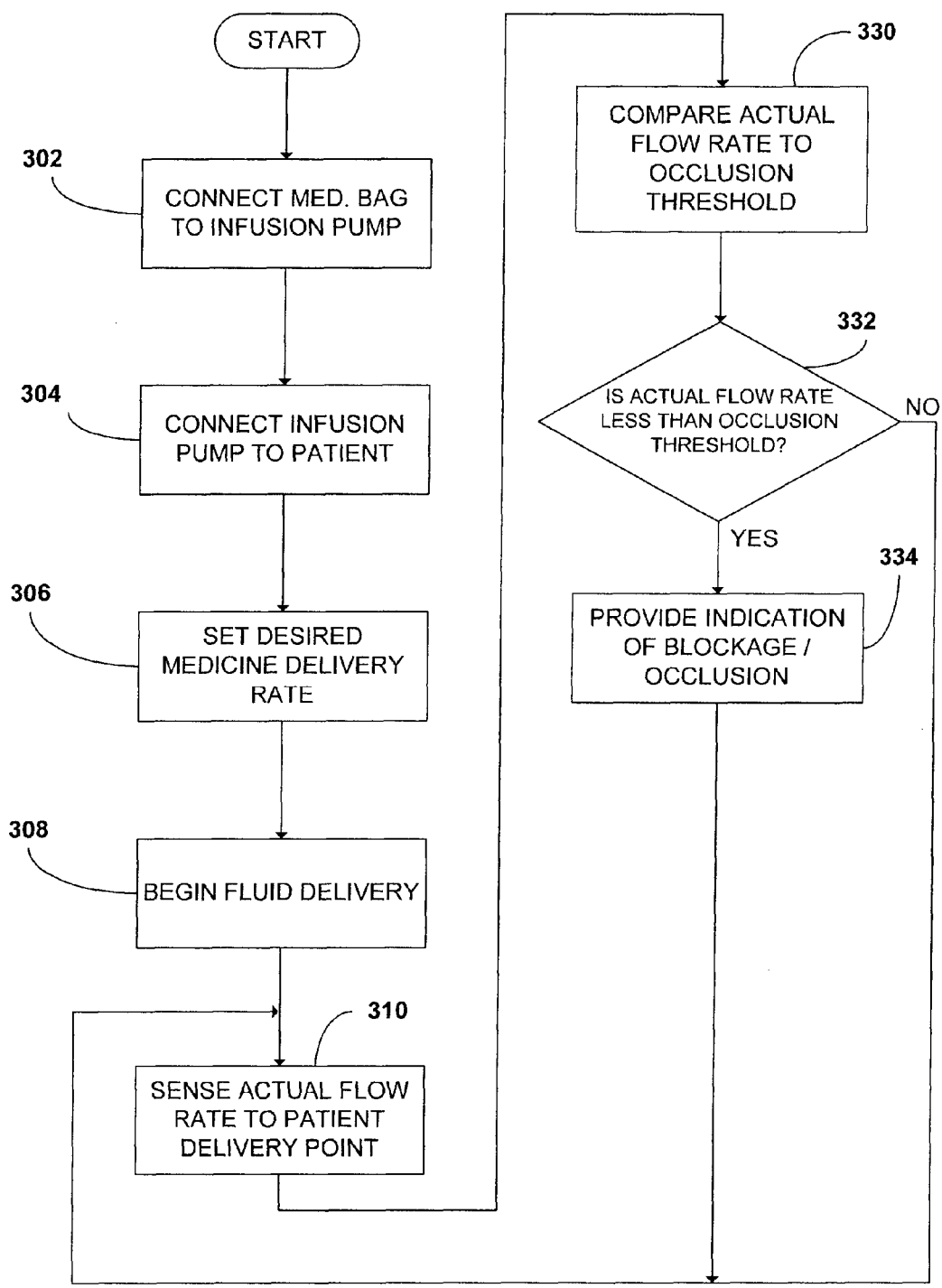
FIG. 3B is a flow chart that illustrates an exemplary method of detecting and reporting a blockage/occlusion in an infusion system, in accordance with aspects of the invention.

FIG. 3B is a flow chart that illustrates an exemplary method of detecting and reporting a blockage/occlusion in an infusion system, in accordance with aspects of the invention. In the illustrated example, the process is similar in several aspects to the method illustrated in FIG. 3A. At block 330, however, the sensed actual flow rate is compared to an occlusion/blockage threshold reference. This threshold tan be a predetermined valve (e.g., a Red number Or a fixed Percentage of the desired delivery rate). Of a dynamically determined value (e.g., a time varying threshold). In the illustrated embodiment, if the sensed actual flow rate is less than the occlusion threshold, a blockage is declared and an alarm condition is. triggered (blocks 332, 334). It should be understood, however, that more complicated comparisons can also be performed. For example, rather than comparing sensed flow rate information against a threshold flow rate value, a change in the sensed flowrate (e.g., a slope) can be determined. If the slope exceeds a slope threshold, a blockage is declared. Further, there may be certain infusion protocols in which zero flow is expected for extended periods of time. In such situations, the controller preferably accounts for this fact.

It should be appreciated that flow rate comparisons (e.g., block 314 or block 330) need not be referenced to a fixed Value. Rather, other flow rate comparisons are possible. Such comparisons include comparing the flow rate to an acceptability range and/or a time varying reference. Further the reference to which the actual flow rate is compared may be programmed by the user or pre-existing and used in connection with an algorithm or treatment protocol.

Figure 4B:
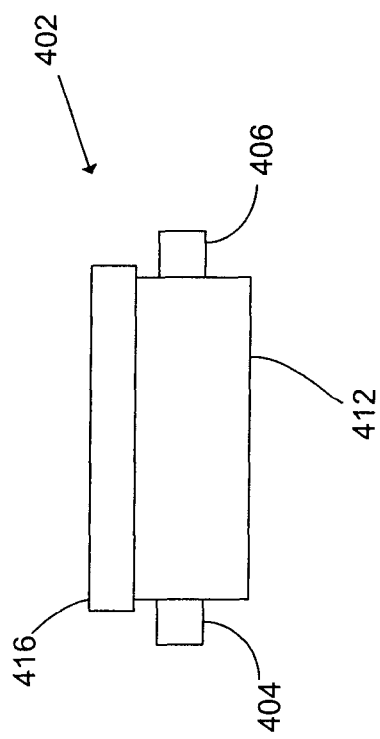
FIG. 4B is a schematic representation of a side view of one embodiment of a flow sensor suitable for use in connection with a closed-loop flow control system, such as the system of in FIG. 2.
Figure 4A:
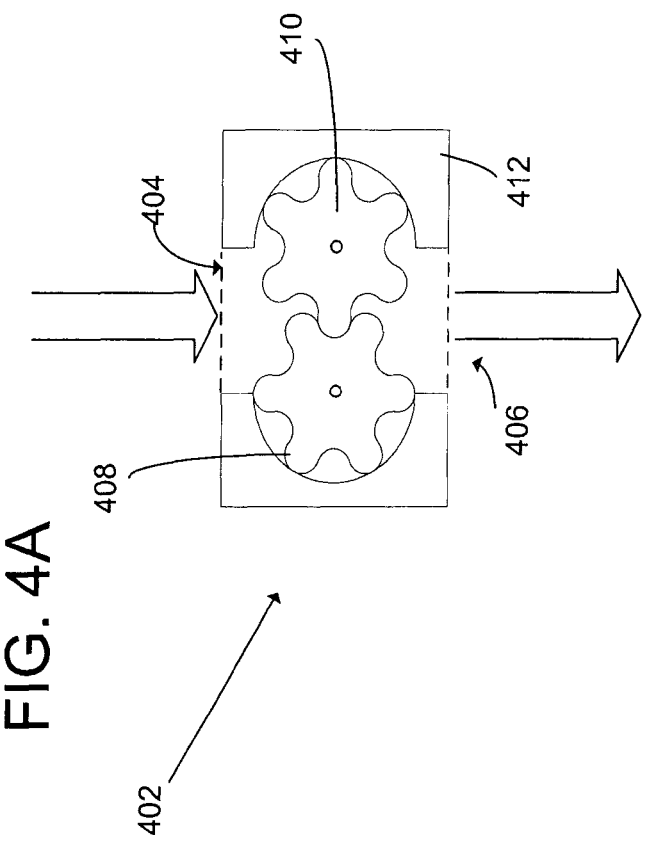
FIG. 4A is a schematic representation of a top view of one embodiment of a flow sensor suitable for use in connection with a closed-loop flow control system such as the system of FIG. 2.

FIGS. 4A and 4B are schematic representations of one embodiment of a flow rate sensor 402 suitable for use in connection with a closed-loop flow control system, such as the pump system 208 illustrated in FIG. 2. Flow rate sensor 402 preferably comprises a micro-fabricated MEMS device or a similar micro-molded device (e.g., an assembly of micro-molded components). Exemplary fabrication techniques for manufacturing such a flow sensor are discussed below. Flow rate sensor 402 has an inlet port 404 and an outlet port 406 and is preferably constructed and arranged to fit in-line with an administration tube (e.g., tube 204 of FIG. 2) such that the fluid flowing in the tube to the patient also flows through sensor 402.

In the illustrated embodiment, flow rate sensor 402 comprises a positive displacement flow sensor. In general, such sensors operate by allowing known volumes of fluid to be transferred during each rotation. The particular flow sensor illustrated comprises a two inter-meshed gears/impellers 408, 410 (sometimes referred to herein as rotors or rotating members). In the illustrated example, each impeller has six lobes, but other sizes and shapes may be used. As illustrated, the impellers are held on pins. Within a housing 412. The housing is preferably sized and shaped for being used in-line with an administration tube (e.g., tube 204 of FIG. 2). In one embodiment, the flow sensor comprises four components: the first impeller 408; the second impeller 410; the housing (including the pins on which the impellers are mounted and rotate); and a cover 416 sized and shaped for sealing the unit such that entry and exit Triust be had via inlet 404 and outlet 406, respectively. The cover, housing, and impellers are also preferably sized and shaped such that substantially all fluid passing through the sensor passes by operation of first and second impellers 408 and 410 in a positive displacement fashion.

The cover 416 may be clear so that the operation of the sensor may tie-monitored by an optical reader. If the flow sensor 402 is constructed primarily out of a silicon or silicon-based material, cover 416 preferably comprises a flat, clear, and heat resistant material, such as, for example Pyrex®. If flow sensor 402 is constructed primarily out of plastic, a flat plastic cover may be used. Laser welding techniques or ultrasonic welding may be used to seal the cap to the base. Preferably, in ultrasonic welding applications, energy directors are also used.

By way of further example, the alignment pins that hold the impellers in place could be part of the cap and/or the base. Further, the base and/or cap could include recessed holes to accept pins that are part of the impellers (i.e., the impellers have pins that extrude from their top or bottom).

In operation, flowing fluid causes impellers 408, 410 to rotate and to transfer a known volume of fluid from the input port 404 side to the outlet port 406 side. Optical or other techniques are used to count rotations (or partial rotations). Such information is indicative of flow rate because each rotation relates to a known volume of fluid. Therefore, flow rate sensor 402 effectively provides a flow rate signal that is indicative of an actual rate of fluid flow through the sensor.

Figure 7:
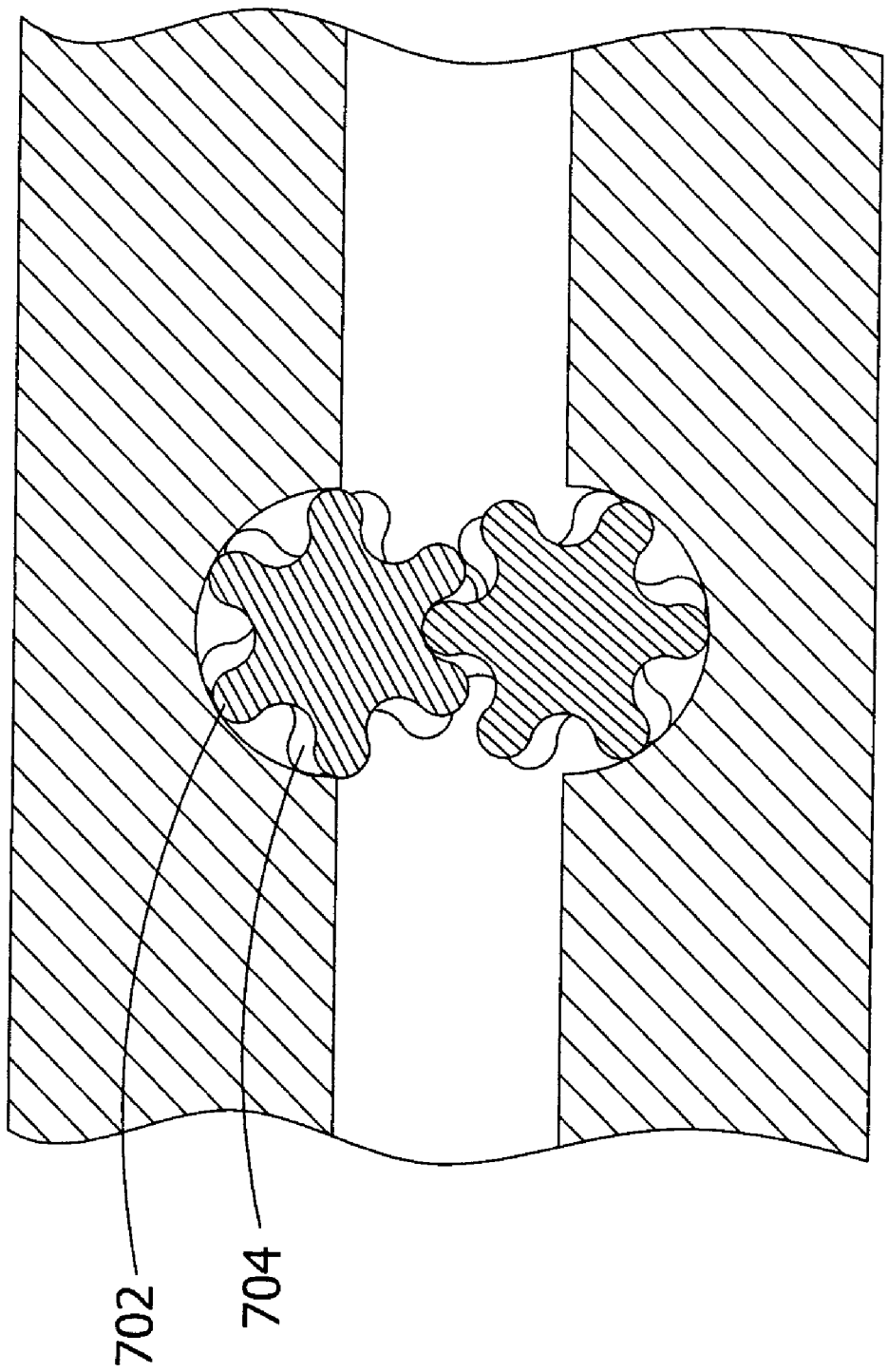
FIG. 7 is a top view of a cap piece, suitable for use in connection with a positive displacement flow rate sensor, in accordance with aspects of the present invention.

One method of providing an optical indication is to mark one or more of the lobes of one or both impellers 408, 410 such that an optical contrast is created. An optical reader then optically detects when the marked lobe has moved, thereby providing an indication of a rotation. Similarly, the reader may be configured to illuminate flow rate sensor 402 (e.g., using an LED) and to thereafter examine the light reflected to detect the output signal (e.g., flow rate signal from flow rate sensor 212 in FIG. 2). In optical detection approaches described herein, the flow sensor itself is preferably passive the reader supplies the light and processes the returned light to provide a signal to the controller. A controller (e.g., controller 232) can use this information to determine an actual flow rate through flow rate sensor 402. This is so because each rotation of the impellers' results in a known volume of fluid passing through the impellers. FIG. 7, which is discussed in greater detail below, illustrates one embodiment of a rotational measurement technique that is particularly suited for use when the flow rate sensor uses a transparent plastic cap.

Other methods of detecting rotation are possible. For example, an impeller can include a magnetic component that generates a detectable magnetic field that changes as the impeller rotates (e.g., an electrical variation caused by the rotation of the impeller). Such a changing magnetic field would provide a flow rate signal that could be detected by, for example, a Hall sensor or similar device.

As another alternative, the reader may be made integral with the flow rate sensor itself. For example, a semiconductor device may be used (e.g., a semiconductor that forms or is part of the cap). The rotation rate is detected electronically by the semiconductor device and the output signal is provided directly to the controller, without the use of a reader that is separate from the flow rate sensor.

In one embodiment, flow rate sensor 402 is constructed using relatively low-cost, precision MEMS and/or micro-molding techniques so that the sensor can be used in connection with a cost-effective, disposable administration set suitable for use in delivering a medical fluid. Thus, the components that do not come directly into contact with the fluid and/or patient (e.g., the pump, controller, and so on) are reusable, while the parts that come into contact with the fluid and/or patient are disposable. In another embodiment, the administration set and infusion pump are both designed to be disposable (e.g., disposed after each use). Two exemplary manufacturing techniques are discussed in greater detail below. It should also be understood that other types of flow sensors and other positive displacement arrangements may be used, and that the illustrated flow rate sensor 402 is provided for exemplary purposes. For-example, other configurations of positive displacement flow sensors may use a different number of-lobes and/or impellers, or have impellers of varying sizes and shapes—including asymmetrical impellers.

Figure 5:
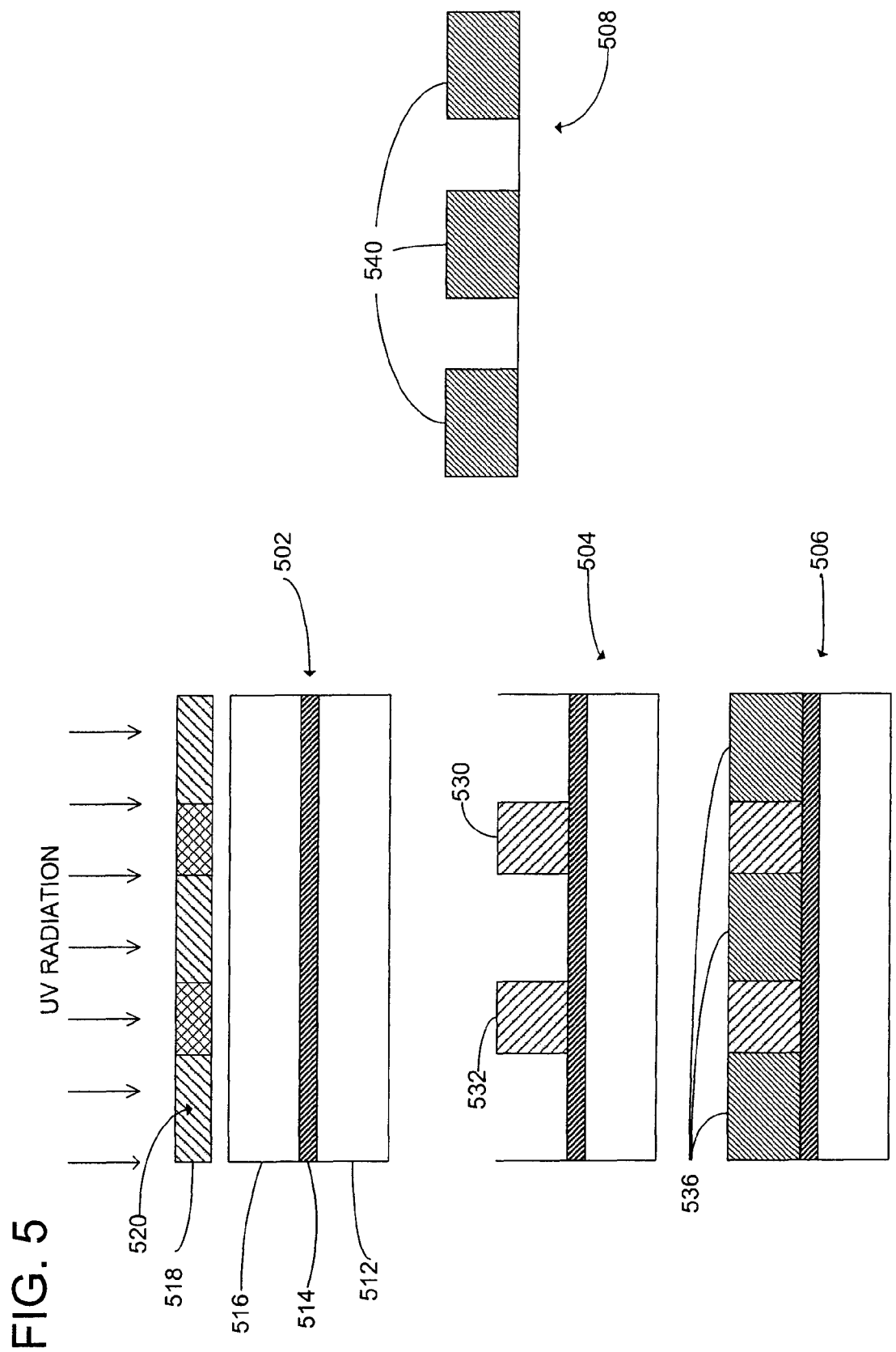
FIG. 5 illustrates an exemplary process of manufacturing a positive displacement flow sensor using a high aspect ratio lithographic process.
Figure 6:
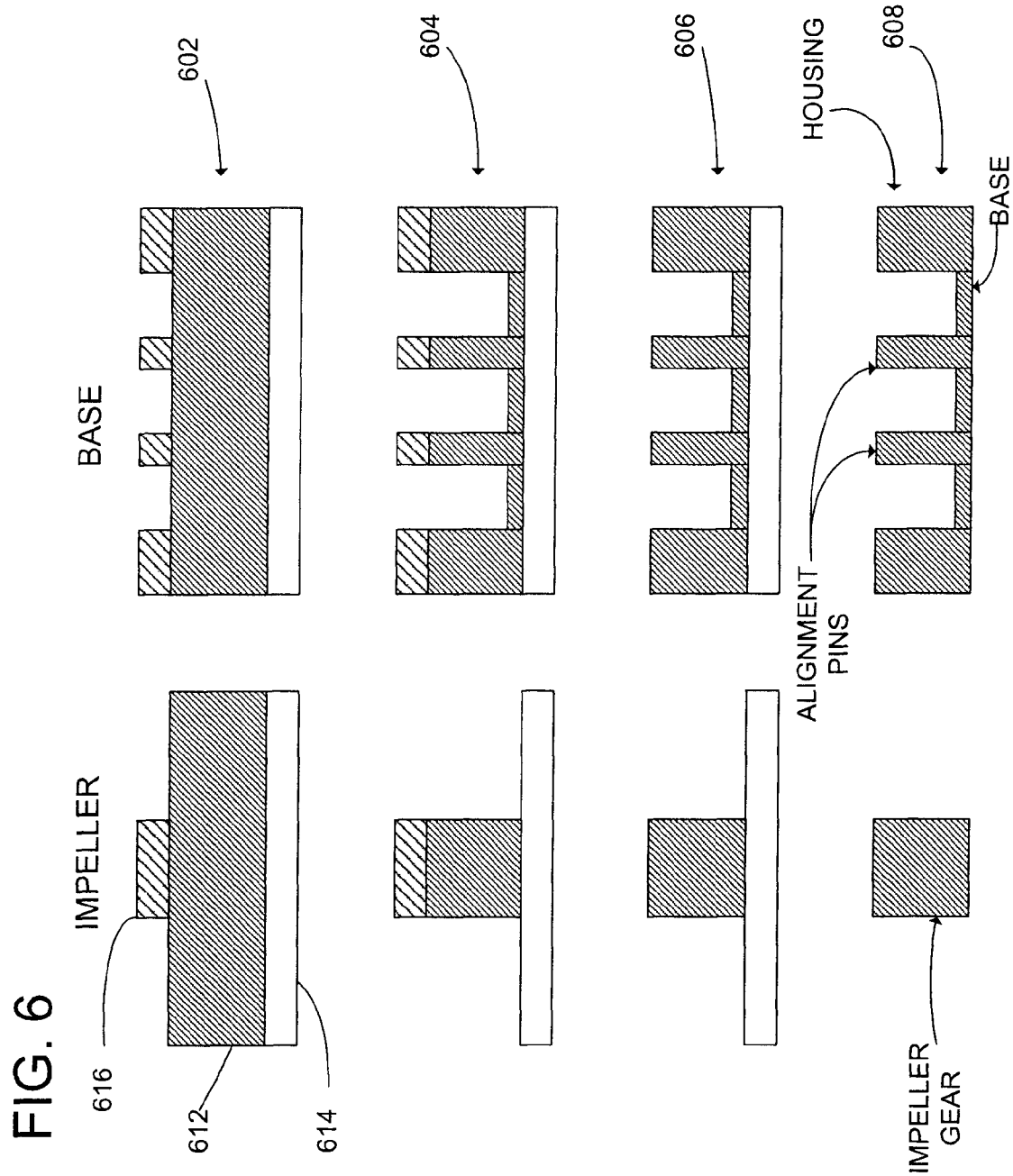
FIG. 6 illustrates an exemplary process of manufacturing a positive displacement flow sensor using a deep reactive ion etching sequence.

FIGS. 5 and 6 illustrate two exemplary methods of manufacturing a flow sensor, such as flow rate sensor 402, suitable for use in connection with-aspects of the present invention. More particularly, FIG. 5 illustrates the pertinent steps of manufacturing a positive displacement flow sensor using a high aspect ratio lithographic process which is sometimes referred to herein as ultra-violet LIGA (UV LIGA) or deep ultra-violet LIGA (DUV LIGA). FIG. 6 illustrates the pertinent steps of manufacturing a positive displacement flow sensor using a deep reactive ion etching sequence (deep RIE).

UV LIGA typically results in plastic parts. Deep RIE uses silicon or silicon carbide. Thus, the materials base for each approach differs. Further, both processes may be used to manufacture parts. The UV LIGA approach, however, may be more advantageously practiced if it is used to create replication masters that are used as molds or mold inserts.

Referring first to FIG. 5, generally stated, the UV LIGA approach comprises four steps 502, 504, 506, and 508. Step 502 involves preparation and exposure. Step 504 involves developing. Step 506 involves electroplating. Step 508 involves removing any remaining photoresist.

At step 502, a mask 510 (e.g., a quartz glass mask with chrome patterns) is placed above a workpiece to be exposed. The workpiece to be exposed comprises a substrate layer 512 (e.g., a silicon wafer). Prior to exposure, a seed layer 514 is attached to the substrate 512 by a deposition process. A photoimageable material, such as an epoxy-based negative photoresist layer 516 (e.g., SU-8) is added on top of substrate 512 (e.g., deposited from a bottle and spin coated). The mask 510 comprises a two-dimensional pattern that is subsequently transferred down to the SU-8 layer. The seed layer 514 is typically nickel, gold, copper, or nickel-ferrite (NiFe). Below seed layer 514 there may also be a "flash" or very thin layer of a refractory metal such as chromium, titanium, Or tantalum to act as an adhesion layer. Typically, the flash layer is on-the order of 50-500 A, and the seed layer is about 400:5000 A. Additional information regarding this process may be found at Chapter 5 of the "Handbook of Microlithography, Micromachining, and Microfabrication, Volume 2 Micromachining and Microfabrication," available from SPIE Press 1997. The photoresist layer is selectively exposed to deep UV radiation through the pattern of mask 510.

At step 504, the exposed photoresist layer 516 is developed. The developing solution is a solvent and generally depends on the photoresist being used and whether the photoresist is a positive or negative tone. This development process removes the portions of photoresist layer 516 that were exposed to the UV radiation, leaving structures 530 and 532. At step 506, the remaining structures electroplated (up from seed-layer 514), filling the exposed portions 536 removed during the development process. At step 508, the remaining portions of the. photoresist (e.g., structures 530, 532) are developed/etched away, leaving the electroplated structures 540, which may be lifted off of the wafer substrate.

It should be appreciated that a number of such electroplated structures 540, of different sizes and shapes, could be simultaneously formed. For example, one structure could correspond to an impeller (e.g., impeller 408 of FIG. 4A), and another structure could correspond to a housing (e.g., housing 412 of FIGS. 4A and 4B). These structures could thereafter be assembled to form a flow sensor of an appropriate size and shape for use in connection with, for example, the various methods and systems described herein. In other words, structures can be formed for a flow sensor housing having an inlet port and an outlet port, and having pins for accepting first and second impellers. In one embodiment, a clear plastic cover is bonded to the top of the housing, thereby ensuring that substantially all fluid flowing into the flow sensor through the inlet port exits the sensor through the outlet port.

It should also be appreciated that, rather than directly using the electroplated structures 540 for construction a desirable flow sensor, the micro-fabrication processes described herein can be used for creating molds or mold inserts (e.g., negative images of the desired structures). One advantage of such a micro-molding approach is that a large number of molds can be made at once, thereby allowing for large-scale production of flow sensor components, without the need for using the UV LIGA process other than for creating the mold. In one embodiment, components may be made of a plastic or similar material that is suitable for use in a medical environment (e.g., disposable). For example, numerous thermoplastic materials could be used (e.g., polycarbonate or liquid crystal polymer) to mold flow sensors from the master.

One advantage Of using UV-LIGA is that it does not require the use of an expensive synchrotron radiation source. As mentioned above, there are relatively few synchrotrons In the world. In contrast, UV sources are more readily available and relatively inexpensive, and masters can be created in most moderately equipped semiconductor clean room environments.

Conventional synchrotron LIGA processes require X-Ray masks. These masks are fabricated by starting with standard quartz/chrome masks, with the desired patterns thereon. The patterns are subsequently transferred onto silicon (which is transparent to synchrotron radiation) in the form of gold or beryllium patterns, which absorb radiation. DUV LIGA, in contrast, uses the standard quartz/chrome mask to directly process the SU-8. Therefore, another advantage of using UV LIGA is that the SU-8 material and mask are believed to be less expensive than comparable materials used in conventional synchrotron LIGA.

Referring next to FIG. 6, illustrated therein at 602, 604, 606, and 608, respectively, are pertinent steps associated with manufacturing a positive displacement flow sensor using a deep RIE micro-fabrication process. In general, deep RIE is a silicon-based process in which deep reactive ion etching is applied to selectively etch away silicon material from the workpiece. The selectivity of the etching process is determined by photolithographic techniques, such as those developed for manufacturing integrated circuits. By its nature, deep RIE provides good verticality, allowing 3-dimension structures to be established from 2-dimension patterns.

Deep RIE provides a suitable process for manufacturing flow. sensors (either directly or by manufacturing micromolds) for use in connection with a closed-loop flow control system and method, in accordance with aspects of the invention. One such flow sensor may be created etching silicon impellers-from one Substrate, and etching an accepting housing from another substrate (or from another part of a single substrate). The housing preferably includes alignment pins positioned for accepting the impeller gears so that a positive displacement arrangement is formed. The housing also preferably includes a base having a landing. The impeller gears are then placed on their respective rotation pins (either manually or by an automated process). A coverslip (e.g., a clear, heat resistant cover material such as Pyrex® is thereafter anodically bonded to the landing on the base. All or part of the impellers and/or base surface may be oxidized to produce a desired optical contrast between the respective surfaces. This optical contrast can be used for Sensing rotation dale impellers.

FIG. 6 illustrates pertinent steps of producing an impeller and a housing for a flow sensor. Beginning at 602, a workpiece is prepared comprising a silicon substrate 612 bonded to a base layer 614. The base layer 614 may comprise any number of materials. In one preferred embodiment, base layer 614 comprises another silicon wafer. This can also be done with many different types of adhesive layers, and photoresist may be used as an adhesive layer. Other substrate materials may be used such as, for example, silicon carbide. A photoresist material 616 is applied on the silicon substrate and then patterned using exposure and development steps. Thus, the photoresist is developed to form a 2-dimensional mask pattern so that etching selectively occurs only where desirable to create the part being produced. This pattern is thereafter transferred down into the base layer (e.g., silicon) using reactive ion etching. Many commonly available photoresist materials are suitable. It should be understood that the 2-dimensional mask pattern could be transferred to an alternate layer, such as a silicon nitride or silicon oxide layer.

Further, a deposited metal could serve as the etch mask. Such a metallic etch mask would be useful in fabricating. relatively tall structures by reactive ion etching techniques. In the etching process, the base layer (e.g., silicon) may be etched at a higher rate than the photoresist layer is being etched (e.g., perhaps 100 times greater). Thus, a photoresist mask may-be rendered effective if the etching process is carried-out extensively to fabricate tall structures (e.g., several hundred microns deep). In fabricating such tall structures, a metallic etch-mask (etched even more selectively than a-photoresist) would be useful.

Referring still to FIG. 6, the photoresist 616 has a 2-dimension shape corresponding to the 3-dimension part being produced. For example, if an impeller is being produced, the photoresist has a 2-dimension shape like that of the desired impeller. The workpiece is selectively exposed and developed so that the exposed silicon is etched away, leaving the base layer, a silicon structure of the desired height and shape, and the photoresist (see 604). Thereafter, the photoresist is stripped away, leaving the base layer and the silicon structure (see 606). Finally, the structure is released from the base. layer (see 608).

In one embodiment of a flow sensor (e.g., a positive displacement flow sensor) manufactured using deep RIE, the silicon parts are coated with a relatively harder material (e.g., silicon nitride, carbon, or diamond) before the sensor is assembled. Silicon is a hard, but brittle material. As such, a coating improves the strength and integrity of the parts. Also, it should be understood that, rather than manufacturing parts directly, deep RIE can be used to fabricate molds for micro-molding flow sensors in a relatively low-cost, high-volume manner.

In one embodiment, a micro-molded or micro-fabricated flow sensor (e.g., a positive displacement flow sensor) is sized and shaped for being placed in-line with an administration tube (e.g., tube 204) as part of a disposable administration set. In another embodiment, such a flow sensor is integrated into an infusion set in which the fluid supply, the pump, the administration tube, the flow sensor, the controller and the reader are all part of a disposable unit.

Finally, although UV LIGA and/or deep RIE are believed to be two preferred methods for manufacturing flow sensors (or molds therefor), other micro-fabrication techniques may be Substituted. These techniques include, for example, synchrotron LIGA and techniques that are not yet available for exploitation.

FIG. 7 is a top view of a cap piece 700, suitable for use in connection with a positive displacement flow rate sensor, in accordance With aspects of the present invention. As explained above, one, method of determining flow rate using a positive displacement flow sensor (e.g., Sensor 402 of FIGS. 4A and 4B) involves optically measuring the rotation of the impellers tubes. For example, a small optical spot is used to mark one of the lobes. A reader detects when the marked lobe passes a given point and can thereby detect the rotation rate of the impeller. Because the flow rate sensor is a positive displacement type sensor, knowledge of the rotation rate corresponds to the actual flow rate. A similar technique involves a detector focused down, into the sensor, that looks for a reflection due to an optical contrast between the base and impeller. If the base is dark and the impeller is relatively light in contrast to the base, most of the reflected light will occur when a lobe passes. Such an approach generally allows a faster detection rate than monitoring a marked lob.

FIG. 7 illustrates an alternative to using an optical spot. As illustrated, the cap piece 700 has imposed thereupon a pattern 702 that replicates one position of the two impellers relative to each other. In one embodiment, pattern 702 is applied to cap piece 700 with additive processes or subtractive. creating a roughened surface. The pattern 702 is selected to provide an optical contrast between pattern 702 and the impellers 704. For example, if the impellers are a shade of white, the imposed pattern 702 is a dark shade. A relatively broad light source is applied from above to illuminate the flow sensor. Light is reflected back from the relatively light impeller lobes when the impellers are exposed from behind pattern 702. Thus, as the impellers rotate, the amount of light reflected back (e.g., to an optical detector) varies as a function of the amount of the impeller 704 that is exposed from under pattern 702. Thus, reflection intensity will rise and fall to denote each partial rotation associated with a lobe. For example, the reflected light intensity will increase/decrease at a known number of cycles per revolution, depending upon the number of lobes, thereby providing an indication of the rotation rate of the sensor. Such an approach allows a less precise optical system to be used because the entire filed may be illuminated.

It is to be understood that the steps described herein are not to be construed as necessarily requiring their performance in the particular order discussed or illustrated. It is also to be understood that additional or alternative steps may be employed. It should be further appreciated that the novel principles and processes disclosed herein are not limited to the particular embodiments illustrated and described. For instance, flow sensors having a "dual layer" nature can be fabricated (e.g., impellers having pins on the bottom). As a more particular example, impellers having pins fabricated on the bottom can be fabricated using DUV LIGA by adding another layer (i.e., another SU-layer after step 506), and thereafter, exposing, developing, and electroplating. It is also possible to reverse the order fabricate pins first and impellers second. Similarly, silicon etching can be used to etch the impellers (or pins). Thereafter, turn the wafer is turned over and attached to a base etch pins (or impellers).

Further, traditional machining fabrication techniques may be employed in connection with aspects of the present invention. In particular, machining can be used in connection with DUV LIGA processing to fabricate features of a mold that are not dimensionally critical. Such features may include, in some embodiments, input and output ports of a positive displacement flow sensor. Similar, in fabricating flow sensors using silicon, a silicon package (e.g., the silicon components and cover slip) can be formed to fit inside a plastic housing that is fabricated by traditional plastic fabrication techniques. Such a plastic housing can include, for example, input and output ports. Other variations are possible.

In view of the above, it will be seen that the several objects of the invention are achieved and other-advantageous results attained.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions and methods without departing from the scope of the invention, it is intended that all matter contained in the above description or shown in the accompanying drawings. Shall be interpreted as illustrative and not in a limiting sense.

What is claimed is:

1. A system for delivering a fluid at a desired flow rate from a reservoir to a delivery point associated with a patient, the system comprising:

a delivery channel between the reservoir and the delivery point through which the fluid is delivered to the patient;

a pump associated with the delivery channel for operatively delivering the fluid to the delivery point at an adjustable output rate;

a flow sensor located along the delivery channel for sensing a flow of the fluid in the delivery channel and for generating a flow rate signal indicative of a rate of flow of the fluid in the delivery channel, the flow sensor comprising:

a housing having an inlet port and an outlet port, the ports being operatively connected to the delivery channel;

a first rotor positioned within the housing between the inlet port and the outlet port, wherein the flow rate signal is based directly on a rotation of the first rotor, the first rotor being arranged to rotate in response to a flow of medical fluid in the delivery channel, the first rotor including a marker indication; and a cover enclosing the housing such that when the medical fluid flows into the inlet port it causes the first rotor to rotate and thereafter the medical fluid exits through the outlet port, the cover having a transparent portion adjacent to the first rotor that enables rotation of the marker indication to be optically detected; and a controller for controlling the pump, the controller causing adjustments to the output rate of the pump as a function of the flow rate signal whereby the desired flow rate is substantially achieved.

2. A system as set forth in claim 1 further comprising a reader associated with the flow sensor and positioned adjacent the first rotor, the reader being constructed and arranged for detecting the rotation of the first rotor and for providing the flow rate signal as a function of the detected rotation of the first rotor.

3. A system as set forth in claim 2 wherein the reader is positioned substantially within the cover.

4. A system as set forth in claim 2 wherein the reader comprises a Hall sensor that senses an electrical signal caused by a rotation of the rotors and provides the flow control signal in response thereto.

5. A system as set forth in claim 2 wherein the reader comprises a light source.

6. A system as set forth in claim 1 wherein the cover comprises a generally transparent cover allowing light to pass through a portion of the cover.

7. A system as set forth in claim 6 wherein the first rotor comprises a plurality of lobes, at least one of the lobes being marked with the marker indication.

8. A system as set forth in claim 6 wherein the cover has a substantially opaque pattern imposed thereon that substantially prevents light from passing through the pattern.

9. A system as set forth in claim 8 wherein the pattern imposed on the cover corresponds to a shape and size of the first rotor.

10. A system as set forth in claim 1 wherein the pump is a peristaltic pump, a piezoelectric pump or a valve pump.

11. A system as set forth in claim 1 wherein the controller provides a closed-loop control path with the pump.

12. A system for delivering a fluid at a desired flow rate from a reservoir to a delivery point associated with a patient, the system comprising:

a delivery channel between the reservoir and the delivery point through which the fluid is delivered to the patient;

a pump associated with the delivery channel for operatively delivering the fluid to the delivery point at an adjustable output rate;

a flow sensor located along the delivery channel, the flow sensor comprising:

a housing having an inlet port and an outlet port, the ports being operatively connected to the delivery channel;

a first rotor positioned within the housing between the inlet port and the outlet port and comprising a plurality of lobes, at least one of the lobes being marked with a marker indication the first rotor being arranged to rotate in response to a flow of medical fluid in the delivery channel;

a generally transparent cover enclosing the housing such that when the medical fluid flows into the inlet port it causes the first rotor to rotate and thereafter the medical fluid exits through the outlet port; and a reader positioned adjacent the first rotor, the reader being constructed and arranged for detecting a rotation of the first rotor based on an optical detection by optically detecting rotation of the marker indication and for providing a signal that is indicative of a rate of the flow of the medical fluid in the delivery channel as a function of the detected rotation of the first rotor; and a controller for controlling the pump, the controller causing adjustments to the output rate of the pump as a function of the flow rate signal whereby the desired flow rate is substantially achieved.

13. A system as set forth in claim 12 wherein the cover has a substantially opaque pattern imposed thereon that substantially prevents light from passing through the pattern.

14. A system as set forth in claim 13 wherein the pattern imposed on the cover corresponds to a shape and size of the first rotor.

15. A system as set forth in claim 12 wherein the reader comprises a light source.

16. A system for delivering a fluid at a desired flow rate from a reservoir to a delivery point associated with a patient, the system comprising:

a delivery channel between the reservoir and the delivery point through which the fluid is delivered to the patient;

a pump associated with the delivery channel for operatively delivering the fluid to the delivery point at an adjustable output rate;

a flow sensor located along the delivery channel for sensing a flow of the fluid in the delivery channel and for generating a flow rate signal indicative of a rate of flow of the fluid in the delivery channel, the flow sensor comprising a rotatable impeller for rotating in response to the flow of the fluid in the administration tube, the flow rate signal comprising an optical indication generated by a rotation of the rotatable impeller;

an optical reader, responsive to the optical indication, for receiving the flow rate signal and providing a flow control signal indicative of the flow rate signal, wherein the optical reader illuminates the flow sensor causing a reflection from the rotatable impeller, wherein the optical indication generated by the rotation of the rotatable impeller comprises a variation in an intensity of the reflection from the rotation of the rotatable impeller; and a controller for controlling the pump, the controller causing adjustments to the output rate of the pump as a function of the flow rate signal whereby the desired flow rate is substantially achieved.

17. A system as set forth in claim 16, wherein the system further comprises a housing disposed around the rotatable impeller, the housing and the rotatable impeller each comprising a pattern, wherein the housing pattern corresponds to the rotatable impeller pattern, and the housing pattern provides an optical contrast to the rotatable impeller.

18. A system as set forth in claim 16, wherein the rotatable impeller comprises a plurality of lobes.

19. A system as set forth in claim 16, wherein the system further comprises a wireless communication channel between the optical reader and the controller, the controller receiving the flow control signal via the wireless communication channel and causing adjustments to the output rate of the pump in response thereto.

20. A system as set forth in claim 16, wherein the pump is a peristaltic pump, a piezoelectric pump or a valve pump.

21. A system as set forth in claim 16, wherein the controller provides a closed-loop control path with the pump.

* * * * *

UNITED STATES PATENT AND TRADEMARK OFFICE
CERTIFICATE OF CORRECTION

PATENT NO. : 8,226,597 B2
APPLICATION NO. : 12/053156
DATED : July 24, 2012
INVENTOR(S) : Jacobson et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1025 days.

Signed and Sealed this
Seventeenth Day of March, 2020

Andrei Iancu
*Director of the United States Patent and Trademark Office*